US005700823A

United States Patent [19]

Hirth et al.

[11] Patent Number: 5,700,823
[45] Date of Patent: Dec. 23, 1997

[54] TREATMENT OF PLATELET DERIVED GROWTH FACTOR RELATED DISORDERS SUCH AS CANCERS

[75] Inventors: Klaus Peter Hirth, San Francisco; Donna Pruess Schwartz, San Mateo; Elaina Mann, Alameda; Laura Kay Shawver, San Francisco, all of Calif.; György Kéri, Budapest, Hungary; István Székely, Dunakeszi, Hungary; Tamás Bajor, Budapest, Hungary; Janis Haimichael, Budapest, Hungary; László Orfi, Budapest, Hungary; Alex Levitzki; Aviv Gazit, both of Jerusalem, Israel; Axel Ullrich; Reiner Lammers, both of München, Germany

[73] Assignees: Sugen, Inc., Redwood City, Calif.; Biosignal L.T.D., Budapest, Hungary; Yissum Research Development Company, Hebrew University of Jerusalem, Jerusalem, Israel; Max-Planck-Gesellschaft zur Forderung der Wissenschaften E.V., Munich, Germany

[21] Appl. No.: 179,570

[22] Filed: Jan. 7, 1994

[51] Int. Cl.$^6$ .......................... A61K 31/42; A61K 31/175
[52] U.S. Cl. .......................... 514/380; 514/378; 514/379; 514/521
[58] Field of Search .................................. 514/378, 379, 514/380, 521

[56] References Cited

U.S. PATENT DOCUMENTS

| 4,284,786 | 8/1981 | Kämmerer et al. | 548/248 |
|---|---|---|---|
| 4,351,841 | 9/1982 | Kämmerer et al. | 548/248 |
| 5,217,999 | 6/1993 | Levitzki et al. | 514/613 |
| 5,532,259 | 7/1996 | Bartlett et al. | 514/378 |
| 5,547,971 | 8/1996 | Weithmann et al. | 514/378 |

FOREIGN PATENT DOCUMENTS

| 3101093 | 1/1993 | Australia | 514/378 |
|---|---|---|---|
| 0413329 | 8/1990 | European Pat. Off. | 514/378 |
| 0520722 | 6/1992 | European Pat. Off. | 514/378 |
| 0537742 | 4/1993 | European Pat. Off. | |
| 0665013 | 8/1995 | European Pat. Off. | |
| 2524929 | 12/1976 | Germany. | |
| 2240104 | 7/1991 | United Kingdom | 514/378 |
| 8704436 | 7/1987 | WIPO. | |
| 9001800 | 10/1990 | WIPO | 514/378 |
| 9203736 | 5/1992 | WIPO | 514/378 |
| 9218481 | 10/1992 | WIPO. | |
| 9202444 | 4/1993 | WIPO. | |
| 9426260 | 11/1994 | WIPO. | |
| 9521613 | 8/1995 | WIPO. | |

OTHER PUBLICATIONS

Andrews et al., *J. Veterinary Med. Assoc.* 202(2):229–249 (1993).
Bartlett et al., *Agents and Actions*, 32:10–21 (1991).
Baselga et al., *J. National Cancer Institute* 85:1327–1332 (1993).
Baudy et al., *J. Med. Chem.*, 36:331–342 (1993).
Bilder et al., *Am. J. Physiol.* 260(Cell Physiol.29):C721–C730 (1991).
Birchall and Harney, *Chem. Abstract* 88:535 (1978).
Bryckaert et al., *Experimental Cell Research* 199:255–261 (1992).
Bustelo and Barbacid, *Science* 256:1196–1199 (1992).
Caraglia et al., *Cancer Immunol. Immunotherapy* 37:150–156 (1993).
Carboni et al., *J. Am. Chem. Soc.*, 80:2838–2840 (1958).
Chen and Okayama, *BioTechniques*, 6:632–638 (1988).
Dati et al., *Oncogene* 5:1001–1006 (1990).
Decker and Lohmann–Matthes, *J. Immunol. Methods*, 15:61–69 (1988).
Ehrlich and Bogert, *J. Org. Chem.*, 12:522–534 (1947).
Ferris et al., *J. Org. Chem.* 44:173–178 (1979).
Floege et al., *Kidney International*, 43S:47–54 (1993).
Fry, et al. *Protein Science* 2:1785–1797 (1993).
Gazit et al., *J. Med. Chem.*, 32:2344–2352 (1989).
Gazit et al., *J. Med. Chem.* 34: 1896–1907 (1991).
Gazit et al., *J. Med. Chem.* 36:3556–3564 (1993).
Gottardis et al., *J. Steroid Biochem.* 30:311–314 (1988).
Gulbins et al., *Science* 260:822–825 (1993).
Hale et al., *J. Clin. Pathol.* 46:149–153 (1993).
Harris et al., *New Engl. J. Medicine* 327(5):319–328 (1992).
Heldin, *EMBO Journal*, 11:4251–4259 (1992).
Hokstra et al., *Experimental Therpeutics* #2455, from 84th Annual Meeting of American Association for Cancer Research, vol. 34 (1993).
Honneger et al., *Cell* 51:199–209 (1987).
Issidorides and Haddadin, *J. Org. Chem.* 31:4067–4068 (1966).
Karameris et al., *Path. Res. Pract.* 189:133–137 (1993).
Koenders et al., *Breast Cancer Research and Treatment* 25:21–27 (1993).
Korzeniewski and Cellewaert, *J. Immunol. Methods*, 64:313–320 (1983).
Lee and Salemnick, *J. Org. Chem.* 40:3608–3610 (1975).
Levitzki, *Biochem. Pharm.* 40:913–918 (1990).
Ley and Seng, *Synthesis* 1975:415–422.
Lyall et al., *J. Bio. Chem.* 264:14503–14509 (1989).
Marshall, E., *Science* 259:618–621 (1993).
Mattar et al. *FEBS* 334:161–164 (1993).
Mosmann, *J. Immunol. Methods* 65:55–63 (1983).
Muller et al., *Mol. Cell. Biol.* 11:1785–1792 (1991).
Ohmichi et al., *Biochemstry* 32:4650–4658 (1993).
Osborne et al., *Cancer Research* 45:584 (1985).
Osherov et al., *J. Biol. Chem.* 268:11134–11142 (1993).
Osherov et al., *J. Cell Biochem.* 517A:237 (1993).

(List continued on next page.)

*Primary Examiner*—Theodore J. Criares
*Attorney, Agent, or Firm*—Lyon & Lyon LLP

[57] ABSTRACT

Method for treating a patient inflicted with a cell proliferation disorder, such as a cancer, characterized by inappropriate PDGF-R activity. The method involves the step of administering to the patient a therapeutically effective amount of a composition described in application.

23 Claims, 11 Drawing Sheets

OTHER PUBLICATIONS

Ozzello and Sordat, *Europ. J. Cancer* 16:553–559 (1980).
Patterson et al., *J. Med. Chem.* 35:507–510 (1992).
Peterson and Barnes, *The Prostate* 22:335–345 (1993).
Piggott et al., *Brit. J. of Neurosurgery* 7:261–265 (1993).
Plate et al., *Laboratory Investigation*, 67:529–534 (1992).
Pollack et al. *J. Neurosurg.* 73:106–112 (1990).
Ren et al., *Science* 259:1157–1161 (1993).
Rendu et al., *Biochemical Pharmacology* 44:881–888 (1992).
Ross, *Nature* 362:801–809 (1993).
Rusch et al. *Cancer Research* 53:2379–2385 (1993).
Rygaard and Povlsen, *Acta path. microbiol. scand.* 77:758–760 (1969).
Schornagel et al., *Biochem. Pharm.* 33:3251–3255 (1984).
Scott et al., *J. Biological Chem.* 22:14300–14305 (1991).
Seibert et al., *Cancer Research* 43:2223–2239 (1983).
Shafie and Grantham, *J. National Cancer Institute* 67:51–56 (1981).
Skehan et al., *J. Natl. Cancer Inst.*, 82:1107–1112 (1990).
Talmadge and Twardzik, *Agents and Actions*, 35S:135–141 (1991).
Ueno et al., *Science*, 252:844–848 (1991).
Wada et al., *Oncogene* 5:489–495 (1990).
Warri et al., *Int. J. Cancer* 49:616–623 (1991).
Yaish et al., *Science* 242:933–935 (1988).
Yoneda et al., *Cancer Research* 51:4430–4435 (1991).
Zeillinger et al., *Clin. Biochem.* 26:221–227 (1993).
Bristol Laboratories Oncology Products, "VePesid (Etoposide) For Injection and Capsules," Dec. 1992.
Kaur, "Tyrphostin induced growth inhibition: correlation with effect on $p210^{bcr-abl}$ autokinase activity in K562 chronic myelogenous leukemia," *Anti–Cancer Drugs* 5:213–222 (1994).
Kovalenko et al., "Selective Platelet–derived Growth Factor Receptor Kinase Blockers Reverse sis–Transformation," *Cancer Research* 54:6106–6114 (1994).
Mattar et al., "Effects of leflunomides active metabolite, A771726, on signal transduction pathways necessary for proliferation," *Immunobiology* 186(1–2):43 (1992) (abstract).

A10

A11

A12

A13

GROUP 1

B10

B11

B12

B13

B14

B15

B16

B17

B18

B19

C10

C11

C13

GROUP 3

GROUP 4

GROUP 5

F10

F11

F12

GROUP 6

GROUP 7

GROUP 8

GROUP 9

J10

J11

GROUP 10

GROUP 11

TREATMENT OF PLATELET DERIVED GROWTH FACTOR RELATED DISORDERS SUCH AS CANCERS

FIELD OF INVENTION

The present invention relates to methods and compositions for treating cell proliferative disorders characterized by inappropriate platelet derived growth factor receptor (PDGF-R) activity.

BACKGROUND OF THE INVENTION

Platelet derived growth factor receptor (PDGF-R) is a transmembrane receptor tyrosine kinase. Ligand binding to the receptor results in dimerization of two receptors generally leading to intermolecular autophosphorylation of each receptor, commonly referred to as autophosphorylation, and activation of the receptor complex.

PDGF, which is a ligand for PDGF-R, is a dimeric protein having two polypeptide chains joined by disulfide bonds. Each polypeptide is either an A chain polypeptide or a B chain polypeptide. Thus, PDGF can have either two A chains, two B chains, or an A and a B chain.

The PDGF-R consists of two isozymes α and β. Both α- and β-containing receptors have been associated with mitogen activity, while only the β-containing receptor has been associated with chemotaxis and actin reorganization (Heldin, C-H, *EMBO Journal* 11: 4251–4259, 1992).

According to Plate et al., *Laboratory Investigation* 4: 529–534, 1992:

> PDGF is a potent growth factor for mesenchymal and neuroectodermal cells. Endothelial cells have been considered nonresponsive to PDGF, but a recent study has shown that PDGF may have a role in angiogenesis during placenta development. In addition, it has been demonstrated, that PDGFR-β is expressed in endothelial cells in inflammatory tissue and glial tumors. This suggests, that PDGF may play a role in vascular functions in pathological conditions. [Citations omitted.]

Heldin, supra, describes the relationship of PDGF and its receptor, and discusses the role of PDGF in cancer, noting that some cancers do not produce PDGF and have central necroses. Heldin states:

> The adverse effects of PDGF in certain diseases, as discussed above, make PDGF antagonists highly desirable. We and others have recently taken several approaches to develop such antagonists. Antibodies against PDGF have proven to be useful for inhibiting both autocrine stimulation in SSV-transformed cells and the atherosclerotic process that occurs after de-endothelialization of the carotid arteries of rats. Moreover, a soluble form of the PDGF receptor has been shown to bind and inactivate PDGF, and could thus be potentially useful for inhibiting PDGF action in vivo.
>
> Another approach would be to design or find agents that compete in an antagonistic manner with PDGF for receptor binding. In order to identify peptides that interfere with PDGF binding, we systematically screened peptides derived from the B-chain sequence. One peptide was found that inhibited PDGF binding and autophosphorylation of α- as well as β-receptors. However, the peptide also showed some cell toxicity and further development will be necessary before peptide antagonists become useful for in vivo studies. Low molecular weight compounds that interfere with receptor binding have been described, e.g., suramin. However, suramin is not specific enough to be clinically useful as a PDGF antagonist. We recently found that another low molecular weight compound, neomycin, at high concentrations inhibited the binding of PDGF-BB to the α-receptor, but did not inhibit binding to the β-receptor. This compound thus represents an antagonist that distinguishes between the two receptor types; however, its low potency makes it unsuitable for use in vivo. Hopefully, the experiences with suramin and neomycin will aid the future design of more potent and specific PDGF receptor antagonists. The design of such antagonists would be much facilitated by the elucidation of the three-dimensional structure of the PDGF-receptor complex.
>
> PDGF antagonistic activity could also be achieved by inhibition of PDGF receptor dimerization. We hypothesized that monomeric PDGF might fail to induce receptor dimerization and might thus have antagonistic activity. Since reduction of PDGF results in loss of receptor binding, we attempted to identify the interchain disulfide bonds in order to mutate these residues and thereby prevent dimerization of the ligand. This turned out to be quite difficult due to the high density of cysteine residues in PDGF. The approach that finally succeeded involved partial reduction of the PDGF molecule using a concentration of dithiothreitol that reduced only the interchain disulfide bonds, and left the intrachain bonds unaffected. By this procedure the second and fourth cysteine residues from the N-terminus were found to form the two interchain bonds in PDGF. Analysis of a PDGF B-chain mutant in which these two cysteine residues had been mutated to serine residues revealed that it retained receptor binding activity. Is it a receptor antagonist? The answer is no, in fact, the monomeric PDGF induced both receptor dimerization and autophosphorylation. This result may indicate that PDGF-induced receptor dimerization is not only a matter of forming a bridge between two receptor molecules: the dimerization may also involve a ligand-induced conformational change of the extracellular domains of the receptors which promotes receptor-receptor interactions. One possible way of achieving an antagonistic effect, which we are currently exploring, is to combine a wild-type PDGF chain with a mutated chain that does not bind to PDGF receptors but can actively prevent dimerization of receptors. [Citations omitted.]

Spada A. P., et al., entitled "Bis Mono- and Bicyclic Aryl and Heteroaryl Compounds Which Inhibit EGF and/or PDGF Receptor Tyrosine Kinase," PCT/US92/03736, mentions the use of certain bis mono and bicylic aryl compounds. According to Spada:

> In accordance with the present invention, there is provided a method of inhibiting abnormal cell proliferation in a patient suffering from a disorder characterized by such proliferation comprising the administration to a patient of an EGF and/or PDGF receptor inhibiting effective amount of a bis mono- and/or bicyclic aryl and/or heteroaryl compound exhibiting protein tyrosine kinase inhibition activity wherein each aryl and/or heteroaryl group is a ring system containing 0–4 hetero atoms, said compound being optionally substituted or polysubstituted.

SUMMARY OF THE INVENTION

The present invention concerns compounds which can inhibit platelet derived growth factor receptor (PDGF-R)

activity, preferably such compounds selectively inhibit such activity, and thereby inhibit cell proliferative disorders. The featured compounds are active on cell cultures to reduce the activity of the PDGF-R. As exemplified by A10 (see FIG. 1a) the preferred compounds are active in inhibiting the growth of tumor cells in vivo and can selectively inhibit PDGF-R.

Many examples of compounds (see FIGS. 1a–i) belonging to the featured groups (see FIGS. 2a–i) are described. Those skilled in the art can obtain other compounds, to inhibit PDGF-R having equivalent or greater activity using the present disclosure as a guide. For example, the assays described herein can be used to readily screen other compounds belonging to the featured groups (see, FIGS. 2a–i) for equivalent activity and thereby facilitate the isolation of compounds which inhibit PDGF-R activity. Using standard assays, the active site of any one of the compounds described below may be determined and other compounds active at the same site determined.

The present application demonstrates that inhibition of PDGF-R activity is useful for treating a proliferative disease, specifically cancer, and thus clearly indicates that compounds described herein can be used in treatment of other proliferative diseases associated with abnormal expression of PDGF-R, for example, blood vessel proliferative disorders and fibrotic disorders characterized by inappropriate PDGF-R activity. Using the present disclosure as a guide, those in the art can readily determine which of the compounds described herein are useful to treat a particular proliferative disease. Thus, applicant defines a single target for a large number of disorders out of the many proposed targets in the art.

Thus, the present invention features methods and compositions for treating cell proliferative disorders characterized by inappropriate PDGF-R activity. Inappropriate activity of PDGF-R reflects the presence of abnormal levels of PDGF or increased expression of PDGF-R. Cell proliferative disorders characterized by such in-appropriate activity can be treated by the compositions and methods of the present invention.

"Cell proliferative disorders" refer to disorders wherein unwanted cell proliferation of one or more subset of cells in a multicellular organism occurs resulting in harm (e.g., discomfort or decreased life expectancy) to the multicellular organism. Cell proliferative disorders can occur in different types of animals and in humans. Cell proliferative disorders include cancers, blood vessel proliferative disorders, and fibrotic disorders.

The methods and compositions are designed to inhibit unwanted cell proliferation by altering the activity of the PDGF-R. Without being bound to any theory, inhibition of unwanted cell proliferation may be brought about by altering the activity of the PDGF-R (e.g., by inhibiting tyrosine phosphorylation of PDGF-R or by inhibiting substrate or adaptor protein binding to the receptor), thereby inhibiting the activity of the PDGF-R. However, unless otherwise stated, the use of the claimed methods and compositions are not limited to this particular theory.

"Inappropriate PDGF-R activity" refers to either 1) PDGF-R expression in cells which normally do not express PDGF-R; 2) PDGF expression by cells which normally do not express PDGF; 3) increased PDGF-R expression leading to unwanted cell proliferation; 4) increased PDGF expression leading to unwanted cell proliferation; or 5) mutations leading to constitutive activation of PDGF-R. The existence of inappropriate or abnormal PDGF and PDGF-R levels or activities is determined by procedures well known in the art.

Unwanted cell proliferation can result from inappropriate PDGF-R activity occurring in different types of cells including cancer cells, cells surrounding a cancer cell, endothelial and smooth muscle cells. For example, an increase in PDGF-R activity of endothelial cells surrounding cancer cells may lead to an increased vascularization of the cancer cell, thereby facilitating growth of the cancer cell.

Compounds (also referred to herein as "drugs") useful in this invention belong to at least eight different groups. The preferred compounds of these groups, and in other as yet undefined groups, that have generally exhibited significant inhibition of PDGF receptor activity are shown in FIGS. 1a–i. While generic formulae are presented, those in the art will recognize that those compounds useful in the invention can be determined by routine screening procedures. Only those compounds active in inhibiting a cell proliferative disorder in vivo or alleviating the phenotype of a proliferation disorder are claimed herein.

The compositions can be used to treat a cell proliferative disorder by administering a therapeutically effective amount of the composition to a patient (i.e. a human or an animal having a cell proliferative disorder). A "therapeutically effective amount", in reference to the treatment of a cancer refers to an amount sufficient to bring about one or more or the following results: reduce the size of the cancer, inhibit the metastasis of the cancer, inhibit the growth of the cancer, stop the growth of the cancer, relieve discomfort due to the cancer, or prolong the life of a patient inflicted with the cancer. The compositions may also be used in in vitro studies of the mechanism of action of the PDGF-R or PDGF itself.

A "therapeutically effective amount", in reference to the treatment of a cell proliferative disorder other than a cancer refers to an amount sufficient to bring about one or more of the following results: inhibit the growth of cells causing the disorder, relieve discomfort due to the disorder, or prolong the life of a patient suffering from the disorder.

Examples are provided below illustrating the ability of various compounds to inhibit PDGF-R phosphorylation. Examples are also provided illustrating the ability of the compound termed A10 (see FIG. 1a) to inhibit cancers in vivo. These examples are not intended to limit the invention. Rather, using the present disclosure as a guide one skilled in the art can use the featured methods and compositions to obtain additional inhibitory compounds and to target other cell proliferative disorders characterized by an inappropriate PDGF-R activity.

Thus, a first aspect of the present invention features a method for treating a patient inflicted with a cancer cell characterized by inappropriate PDGF-R activity. The method involves the step of administering to the patient a therapeutically effective amount of a composition comprising a compound illustrated in FIG. 2 a-i, or the active product formed when any such compound is placed under physiological conditions (i.e., the active structural entity of a pro-drug described above).

Preferably, the compound is either A10, A11, A12, B10, B11, B12, B13, B14, B15, B16, B17, B18, B19, C10, C11, D11, D12, D13, D14, D15, D16, D17, E10, E11, E12, E13, E14, E15, E16, F10, F11, F12, G10, G11, G12, G13, G14, G15, G16, G17, G18, G19, G20, G21, G22, H12, I10, or the active drug of such compounds, or pharmaceutically acceptable salts thereof. The compound is preferably used in a pharmaceutical composition formed by mixing one of the above compounds and a physiological acceptable carrier.

A physiological acceptable carrier is a formulation to which the compound can be added to dissolve or otherwise facilitate administration of the compound. Examples of physiological acceptable carriers include water, saline, physiologically buffered saline, cyclodextrins and PBTE:-D5W. Hydrophobic compounds such as A10 are preferably administered using a carrier such as PBTE:D5W. An important factor in choosing an appropriate physiological acceptable carrier is choosing a carrier in which the compound remains active or the combination of the carrier and the compound produces an active compound. The compound may also be administered in a continuous fashion using a slow release formulation or a pump to maintain a constant or varying drug level in a patient.

In related aspects, the invention features methods for treating a patient having a cell proliferation disorder characterized by inappropriate PDGF-R activity. The methods include the step of administering to a patient a sufficient amount of a composition to reduce inappropriate PDGF-R activity. The composition comprises one of the featured compounds or a mutated PDGF-R, or nucleic acid encoding a mutated PDGF-R. "Mutated" PDGF-R refers to PDGF-R wherein one or more amino acid is missing or altered. As illustrated below a nucleic acid encoding a mutated (i.e., a truncated) PDGF-R lacking a kinase domain can inhibit tumor growth in vivo. Mutated PDGF-R can be administered as a protein, or recombinant nucleic acid encoding the protein and expressing the protein inside a cell.

In other aspects, the invention features novel compositions including one of the featured compounds herein described and PBTE:D5W carrier where the featured compound is soluble in PBTE:D5W; and the novel compounds B10, B12, C10, C11, E10, E11, E12, E13, E14, E15, E16, F10, F11, F12, G21, G22, H11, H12, H13, and H14.

Other features and advantages of the invention will be apparent from the following description of the preferred embodiments thereof, and from the claims.

DETAILED DESCRIPTION OF THE INVENTION

Figure 1A:
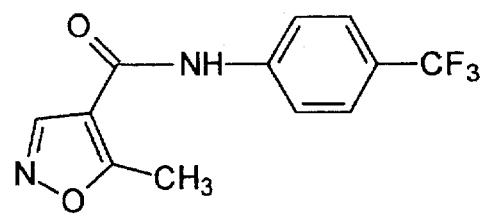
FIGS. 1a–k illustrate the chemical structures of the preferred compounds.
Figure 1A:
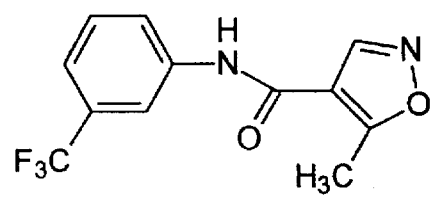
Figure 1A:
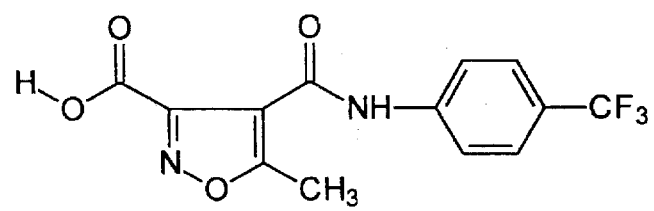
Figure 1A:
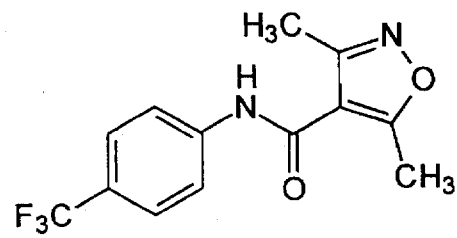

The present invention features methods and compositions for treating cell proliferative disorders characterized by inappropriate PDGF-R activity. One preferred compound is A10 (see FIG. 1a) or the drug produced therefrom in vivo, B11 (also known as A77 1726).

The ability of A10, truncated versions of a PDGF-R and other compounds to inhibit tumor growth in animals illustrates the effectiveness and efficacy of these compounds. Such animal studies support the effectiveness of the compounds by demonstrating that the compounds can be effective in animals despite various problems which are inherently associated with using compounds in animals to treat a particular ailment. The inherent problems include the animal being comprised of a heterogeneous cell population, various pharmacological considerations such as bioavailability of the compound, the half life of the compound, and clearance of the compound. These inherent problems often prevent a compound from exerting a physiological effect.

PDGF-R Activity

Ligand binding to the PDGF-R induces the formation of receptor dimers and allosteric changes that activate the intracellular kinase domains, and result in the transphosphorylation of the receptor on tyrosine residues. Receptor phosphorylation stimulates a physical association of the activated receptor with target molecules, via conserved SH2 domains. Some of the target molecules are in turn phosphorylated, which transmits the signal to the cytoplasm. Other target molecules are not phosphorylated, but assist in signal transmission by acting as docking or adapter molecules for secondary signal transducer proteins. The secondary signal transducer molecules generated by activated receptors results in a signal cascade that regulates cell functions such as cell division. (See, Fry M. J. et al., *Protein Science* 2: 1785–1797, 1993)

Thus, an increase in PDGF-R activity is characterized by an increase in one or more of the activities which can occur upon PDGF-R ligand binding: (1) autophosphorylation of PDGF-R, (2) phosphorylation of a PDGF-R substrate (e.g., PL 3-kinase, RasGAP, PLCγ, see Fry supra), (3) activation of an adapter molecule, and (4) increased cell division. These activities can be measured using techniques described below and known in the art. For example autophosphorylation of PDGF-R can be performed as described in the examples below using an anti-phosphotyrosine antibody, and increased cell division can be performed as described below by measuring $^3$H-thymidine incorporation into DNA. Preferably, the increase in PDGF-R is characterized by an increased amount of phosphorylated PDGF-R and DNA synthesis.

Featured Compounds

Compounds of groups 1 to 9 are shown in FIGS. 2a–i. Group 1 compounds have the basic structure shown in FIG. 2a, where $R_1$, $R_2$, $R'_2$, $R''_2$, and $R'''_2$ are independently selected from the group consisting of hydrogen, halogen, trihalomethyl, and $NO_2$; preferably $R_1$ and $R_2$ are independently $CF_3$, $NO_2$ or hydrogen, and $R'_2$, $R''_2$, and $R'''_2$ are hydrogen; and $R_3$ is selected from the group consisting of hydrogen, carboxy, or carbalkoxy. Examples of group 1 compounds are listed in Table I and shown in FIG 1a.

TABLE I

| Compound | $R_1$ | $R_2$ | $R_3$ |
| --- | --- | --- | --- |
| A10 | $CF_3$ | H | H |
| A11 | H | $CF_3$ | H |
| A12 | $CF_3$ | H | Carboxy |

These compounds are believed to act as prodrugs in that the ring is cleaved in vivo to yield active metabolites.

Figure 1B:
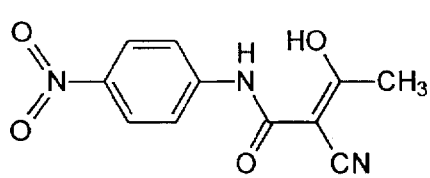
Figure 1B:
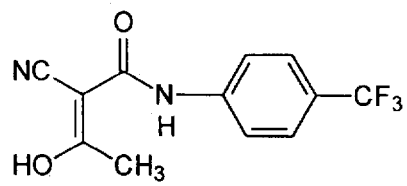
Figure 1B:
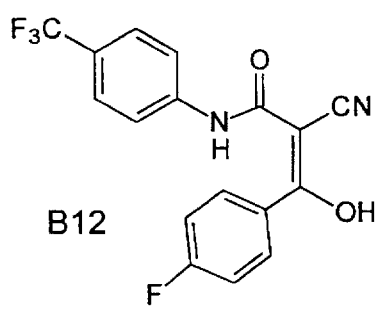
Figure 1B:
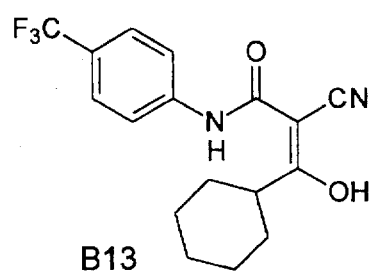
Figure 1B:
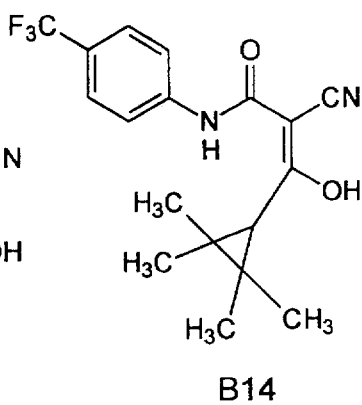
Figure 1B:
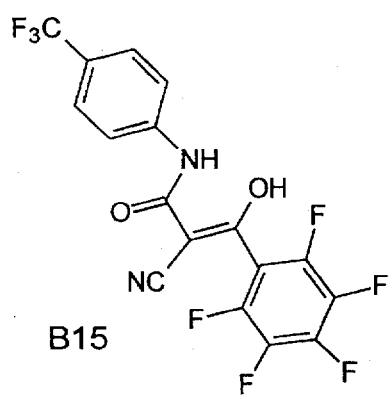
Figure 1B:
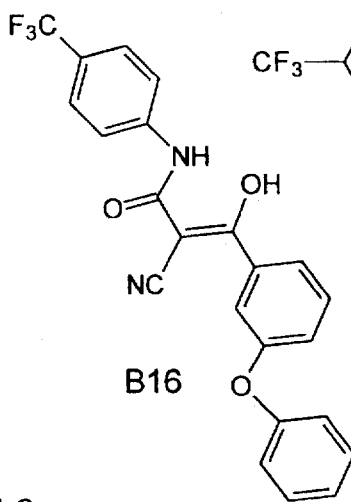
Figure 1B:
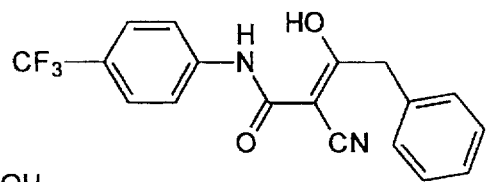
Figure 1B:
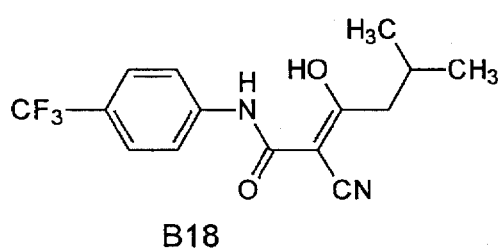
Figure 1B:
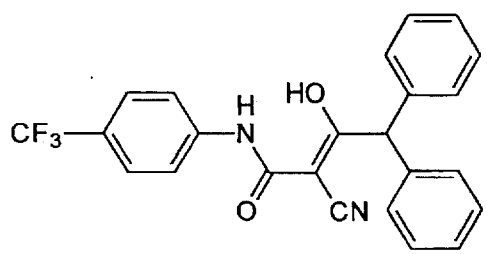
Figure 2A:
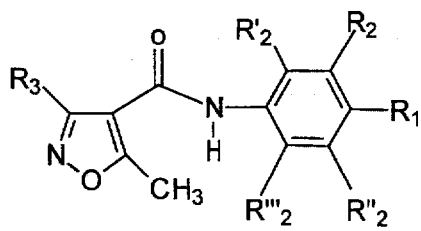
FIGS. 2a–i illustrate the generic chemical structure of groups 1–8 respectively.
Figure 2B:
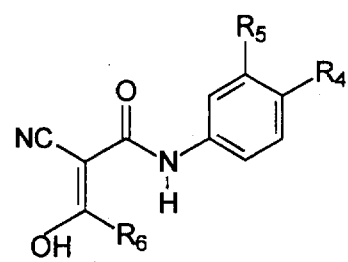

Group 2 compounds have the basic structure shown in FIG. 2b, where $R_4$ and $R_5$ are independently halogen, hydrogen, trihalomethyl, or $NO_2$; preferably $R_4$ is $CF_3$ and $R_5$ is H; $R_6$ is either aryl, alkyl, alkenyl, or alkynyl; preferably $R_6$ is one of the substituents of the compounds listed in Table II. Examples of group 2 compounds are listed in Table II and shown in FIG. 1b.

TABLE II

| Compound | $R_4$ | $R_5$ | $R_6$ |
| --- | --- | --- | --- |
| B10 | $NO_2$ | H | $CH_3$ |
| B11 | $CF_3$ | H | $CH_3$ |
| B12 | $CF_3$ | H | 4-fluorophenyl |
| B13 | $CF_3$ | H | cyclohexyl |
| B14 | $CF_3$ | H | 2,2,3,3-tetramethyl-cyclopropyl |
| B15 | $CF_3$ | H | pentafluorophenyl |

TABLE II-continued

| Compound | $R_4$ | $R_5$ | $R_6$ |
| --- | --- | --- | --- |
| B16 | $CF_3$ | H | 3-phenoxy-phenyl |
| B17 | $CF_3$ | H | benzyl |
| B18 | $CF_3$ | H | 2-methylpropyl |
| B19 | $CF_3$ | H | diphenylmethyl |

Figure 1C:
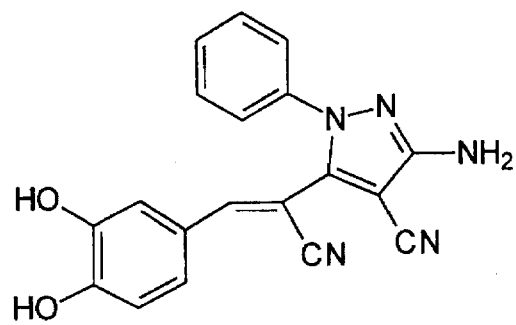
Figure 1C:
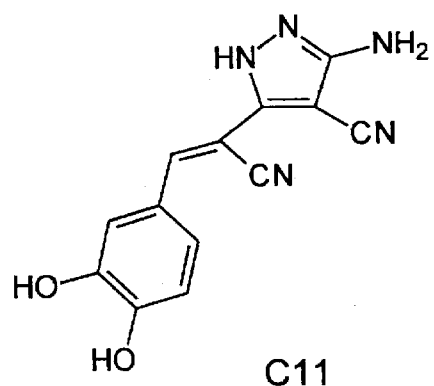
Figure 1C:
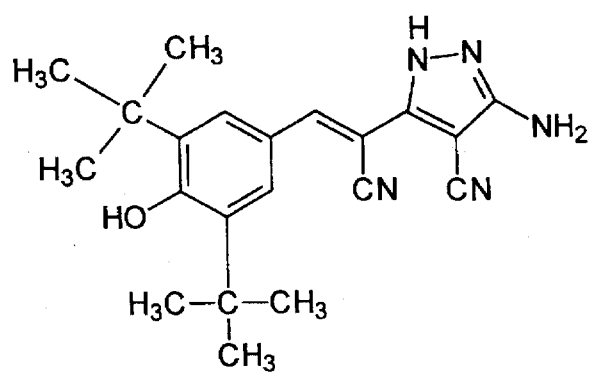
Figure 2C:
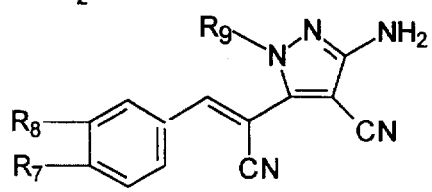

Group 3 compounds have the structure shown in FIG. 2c, where $R_7$ and $R_8$ are independently halogen, OH, hydrogen, alkoxy, SH, or $NH_2$, preferably $R_7$ and $R_8$ are OH; $R_9$ is aryl or hydrogen, preferably hydrogen or phenyl. Examples of group 3 compounds are listed in Table III and shown in FIG. 1c.

TABLE III

| Compound | $R_7$ | $R_8$ | $R_9$ |
| --- | --- | --- | --- |
| C10 | OH | OH | phenyl |
| C11 | OH | OH | H |

Figure 1D:
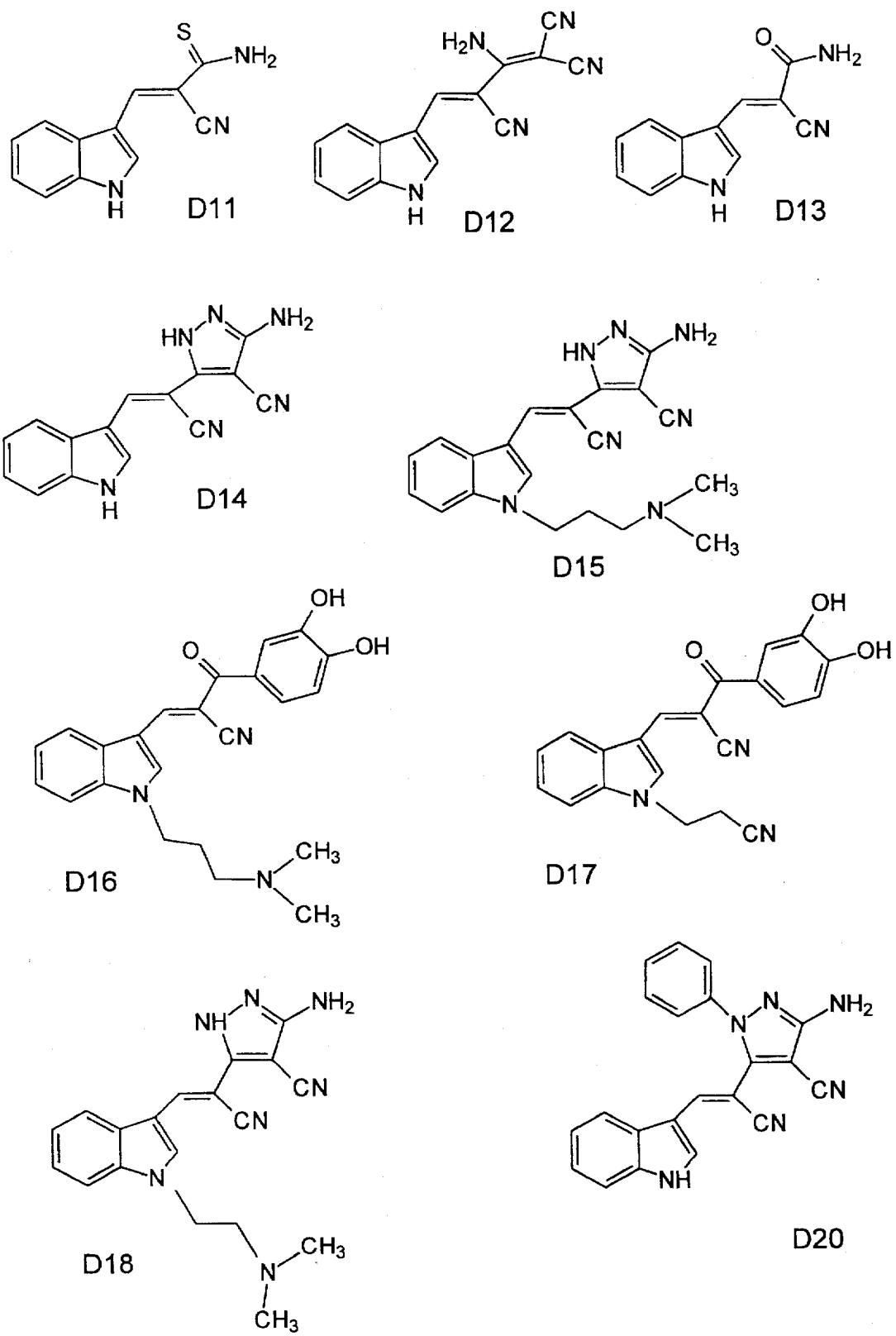
Figure 2D:
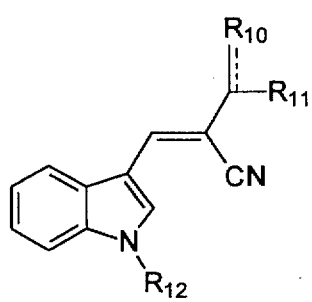

Group 4 compounds have the structure shown in FIG. 2d, where $R_{10}$ is either =S, =O, SH, OH, or $NH_2$; and $R_{11}$ is SH, OH, $NH_2$, =C(CN)$_2$ or aryl, preferably $NH_2$, =C(CN)$_2$, or dihydroxyl-phenyl; or $R_{10}$ and $R_{11}$ taken together are aryl, preferably 3-amino-4-cyano-5-pyrazole; and $R_{12}$ is hydrogen, aryl, alkyl, alkenyl, or alkynyl, preferably hydrogen, —(CH$_2$)$_2$CN$_2$ or —(CH$_2$)$_2$N(CH$_3$)$_2$. Examples of group 4 compounds are listed in Table IV and shown in FIG. 1d.

TABLE IV

| Compound | $R_{10}$ | $R_{11}$ | $R_{12}$ |
| --- | --- | --- | --- |
| D11 | =S | $NH_2$ | H |
| D12 | $NH_2$ | =C(CN)$_2$ | H |
| D13 | =O | $NH_2$ | H |
| D14 | 3-amino-4-cyano-5-pyrazole | | H |
| D15 | 3-amino-4-cyano-5-pyrazole | | —(CH$_2$)$_2$N(CH$_2$)$_2$ |
| D16 | =O | 3,4-dihydroxyl-phenyl | —(CH$_2$)$_2$N(CH$_2$)$_2$ |
| D17 | =O | 3,4-dihydroxyl-phenyl | —(CH$_2$)$_2$CN$_2$ |

Figure 1E:
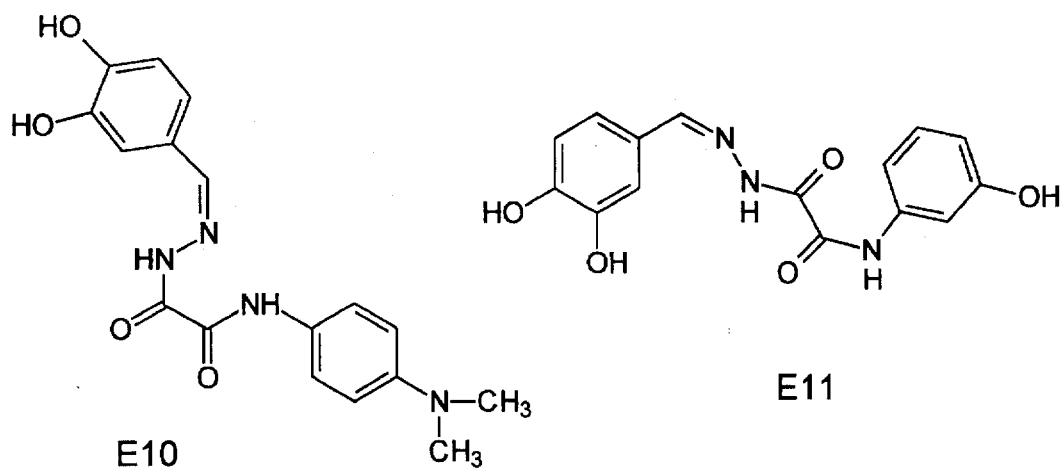
Figure 1E:
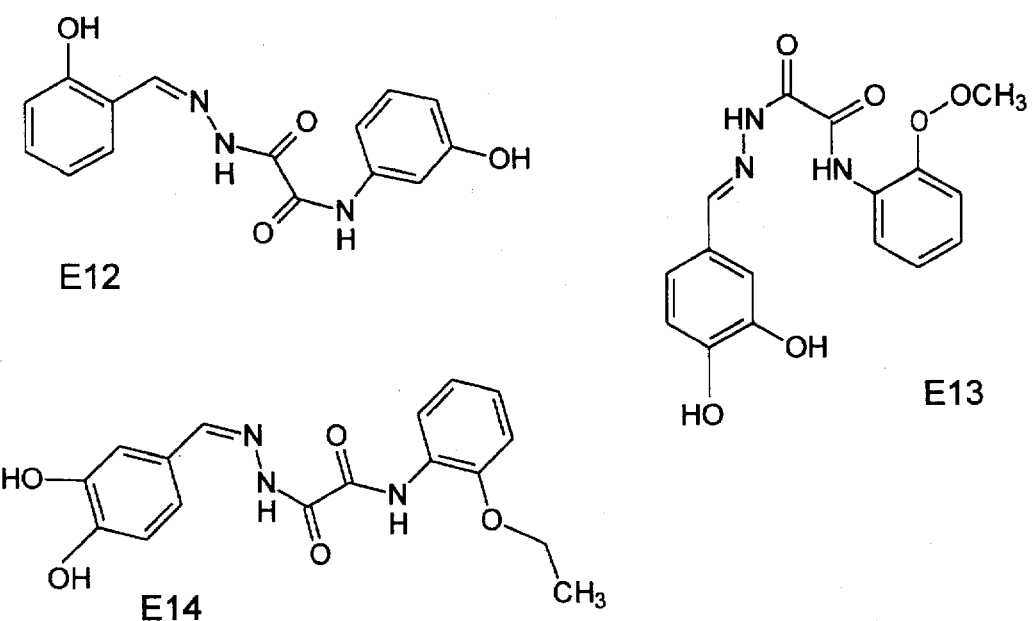
Figure 1E:
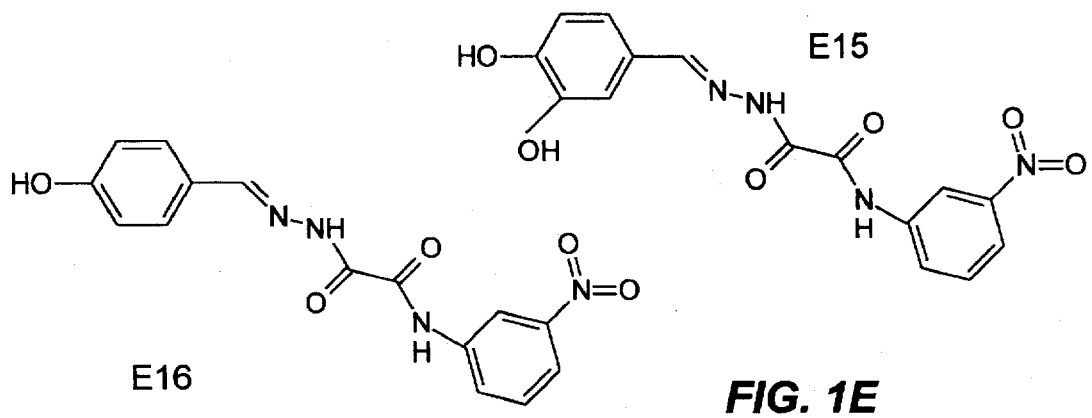
Figure 2E:
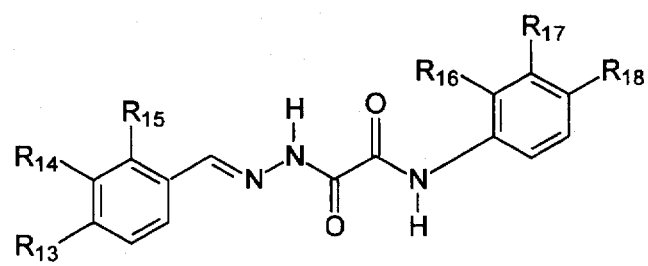

Group 5 compounds have the structure shown in FIG. 2e, where $R_{13}$, $R_{14}$, $R_{15}$, $R_{16}$, $R_{17}$, and $R_{17}$, are independently hydrogen, halogen, alkoxy, OH, amino, alkylamino, or SH; preferably hydrogen or OH. Examples of group 5 compounds are listed in Table V and shown in FIG. 1e.

TABLE V

| Compound | $R_{13}$ | $R_{14}$ | $R_{15}$ | $R_{16}$ | $R_{17}$ | $R_{18}$ |
| --- | --- | --- | --- | --- | --- | --- |
| E10 | OH | OH | H | H | H | N(CH$_3$)$_2$ |
| E11 | OH | OH | H | H | OH | H |
| E12 | H | H | OH | H | OH | H |
| E13 | OH | OH | H | OCH$_3$ | H | H |
| E14 | OH | OH | H | OC$_2$H$_5$ | H | H |
| E15 | OH | OH | H | H | NO$_2$ | H |
| E16 | OH | H | H | H | NO$_2$ | H |

Figure 1F:
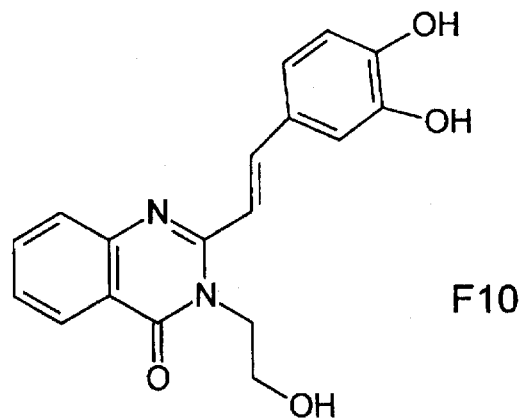
Figure 1F:
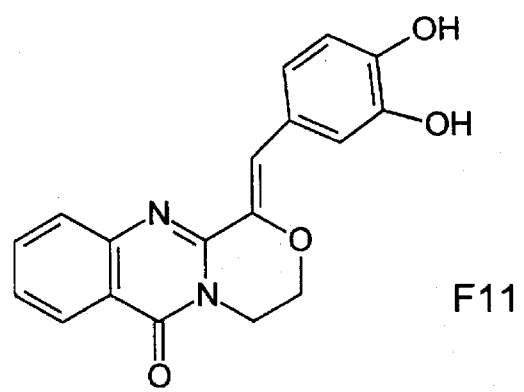
Figure 1F:
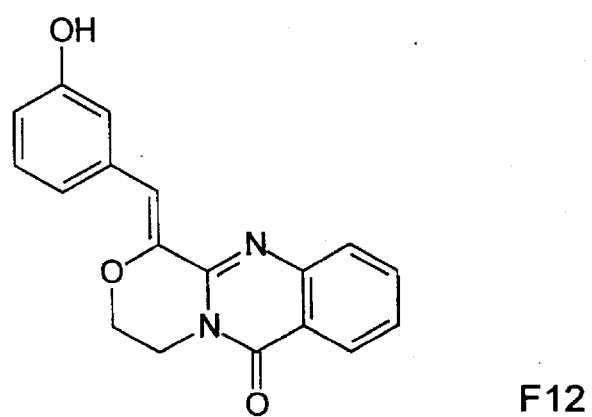
Figure 2F:
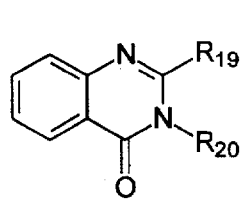

Group 6 compounds have the structures shown in FIG. 2f, where $R_{19}$ is aryl, alkyl, alkenyl or alkynyl preferably 2-(3,4,-dihydroxyphenyl) ethenyl; $R_{20}$ is an alkyl preferably ethylenehydroxy; or $R_{19}$ and $R_{20}$ are together aryl preferably a morpholine ring having a =CH-(mono or dihydroxy-phenyl) substituent. Examples of group 6 compounds are set forth in Table VI and shown in FIG. 1f.

TABLE VI

| Compound | $R_{19}$ | $R_{20}$ |
| --- | --- | --- |
| F10 | (CH$_2$)$_2$OH | CH=CH-3,3-di-hydroxyphenyl |
| F11 | 2-C=CH-(3,4-dihydroxyphenyl)morpholino | |
| F12 | 2-C=CH-(3-hydroxyphenyl)morpholino | |

Figure 1G:
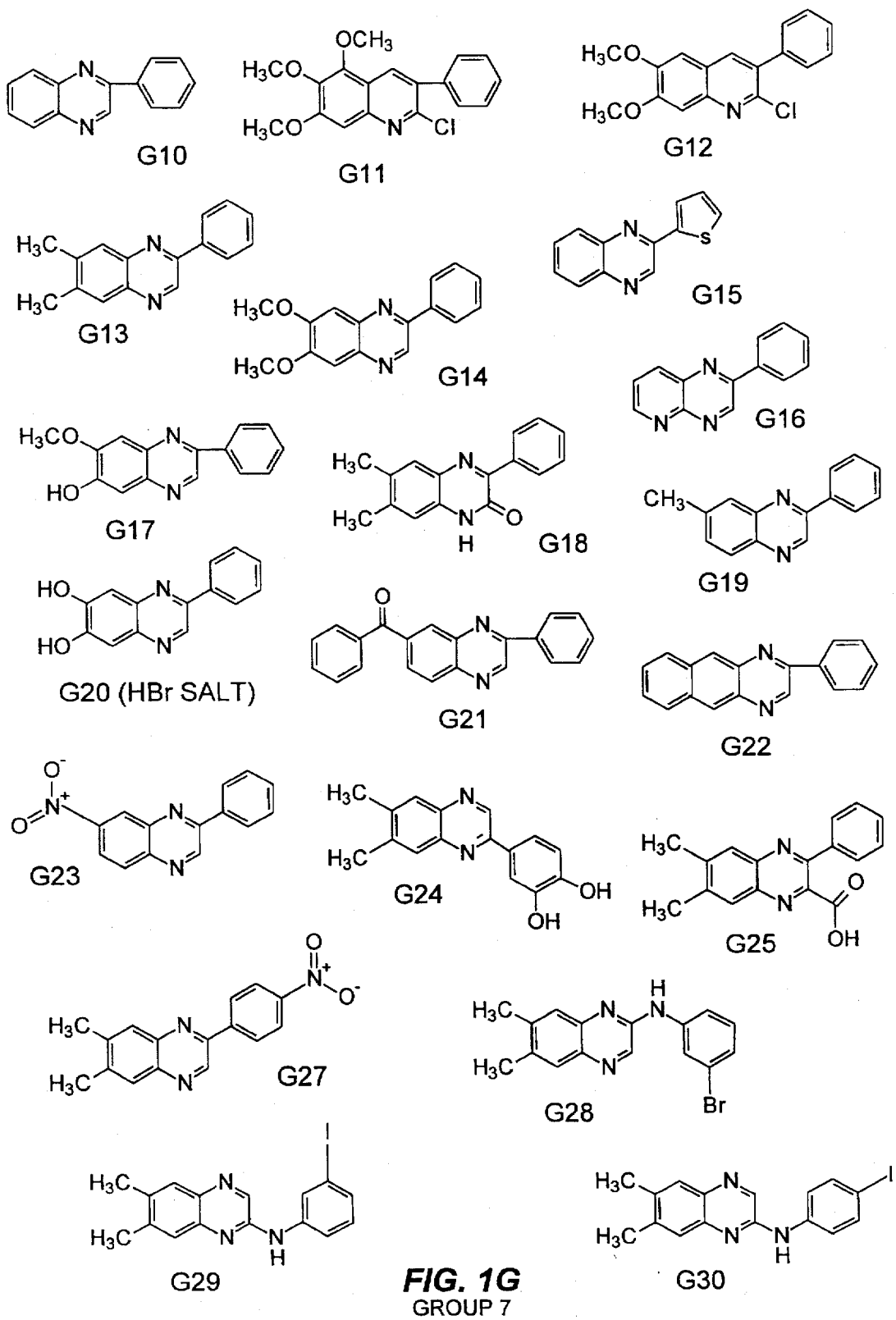
Figure 2G:
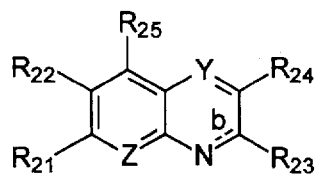

Group 7 compounds have the structures shown in FIG. 2g, where b is an optional pi bond, Y and Z are independently carbon or nitrogen; $R_{21}$ and $R_{22}$, are independently hydrogen, halogen, OH, SH, $NH_2$, alkyl, alkenyl, alkynyl, alkoxy, or benzoyl, preferably OH, CH$_3$, methoxy, or benzoyl, or $R_{21}$ and $R_{22}$ together form an aromatic ring to give an aryl, preferably phenyl; $R_{23}$ is hydrogen, halogen, OH, SH, $NH_2$, or alkoxy; $R_{24}$ is aryl, preferably phenyl or 2-thienyl; $R_{25}$ is hydrogen, halogen, =S, or =O; provided that if b is no bond, the adjacent nitrogen optionally has a substituent selected from the consisting of hydrogen, alkyl, alkyleneamino, alkyleneaminoalkly, and alkylenecyano. Examples of group 7 compounds are set forth in Table VII and shown in FIG. 1g.

TABLE VII

| Compound | b | Y | Z | $R_{21}$ | $R_{22}$ | $R_{23}$ | $R_{24}$ | $R_{25}$ |
| --- | --- | --- | --- | --- | --- | --- | --- | --- |
| G10 | bond | N | C | H | H | H | phenyl | H |
| G11 | bond | C | C | OCH$_3$ | OCH$_3$ | OCH$_3$ | phenyl | Cl |
| G12 | bond | C | C | OCH$_3$ | OCH$_3$ | H | phenyl | Cl |
| G13 | bond | N | C | CH$_3$ | CH$_3$ | H | phenyl | H |
| G14 | bond | N | C | OCH$_3$ | OCH$_3$ | H | phenyl | H |
| G15 | bond | N | C | H | H | H | 2-thienyl | H |
| G16 | bond | N | N | H | H | H | phenyl | H |
| G17 | bond | N | C | OH | OCH$_3$ | H | phenyl | H |
| G18 | no bond | N | C | CH$_3$ | CH$_3$ | =O | phenyl | H |
| G19 | bond | N | C | H | CH$_3$ | H | phenyl | H |
| G20 | bond | N | C | OH | OH | H | phenyl | H |
| G21 | bond | N | C | H | benzoyl | H | phenyl | H |
| G22 | bond | N | C | phenyl | H | H | phenyl | H |

Figure 1H:
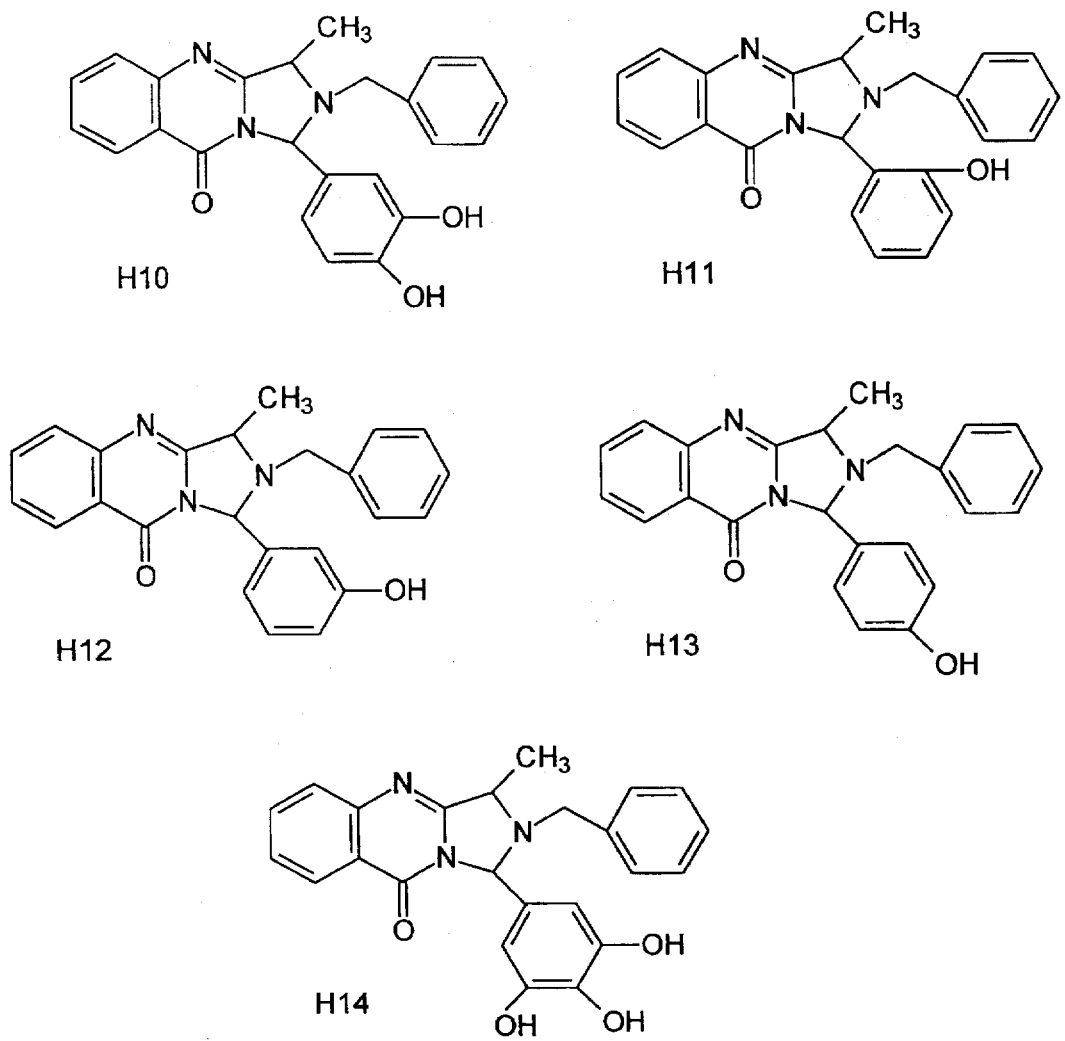
Figure 2H:
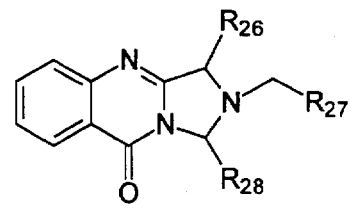
Figure 2I:
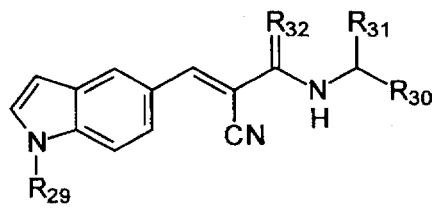

Group 8 compounds have the structure shown in FIG. 2h, where $R_{26}$ and $R_{28}$ is independently alkyl, aryl, alkenyl, or alkynyl; $R_{27}$ is alkyl. Examples of group 8 compounds are set forth in Table VIII and shown in FIG. 1h.

TABLE VIII

Figure 1I:
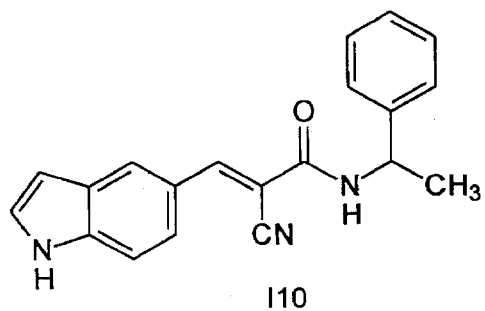
Figure 1J:
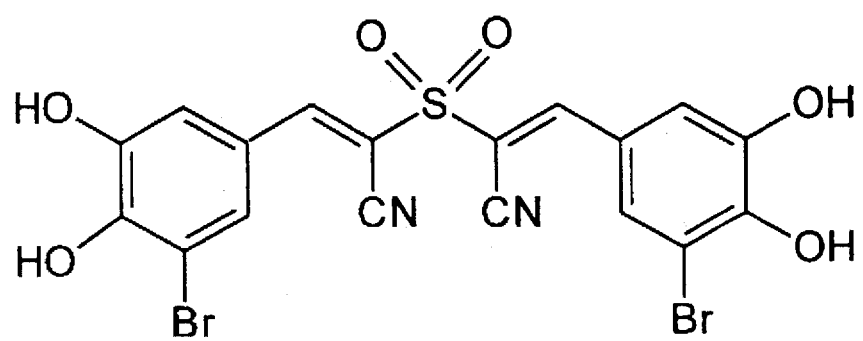
Figure 1J:
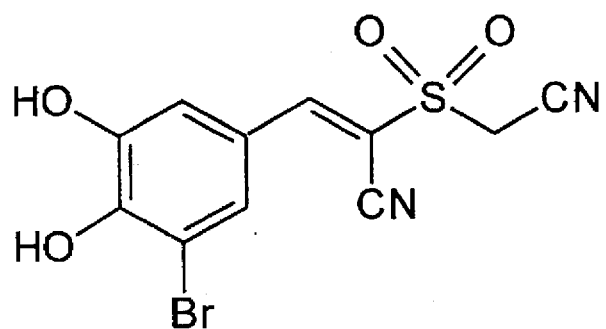
Figure 1K:
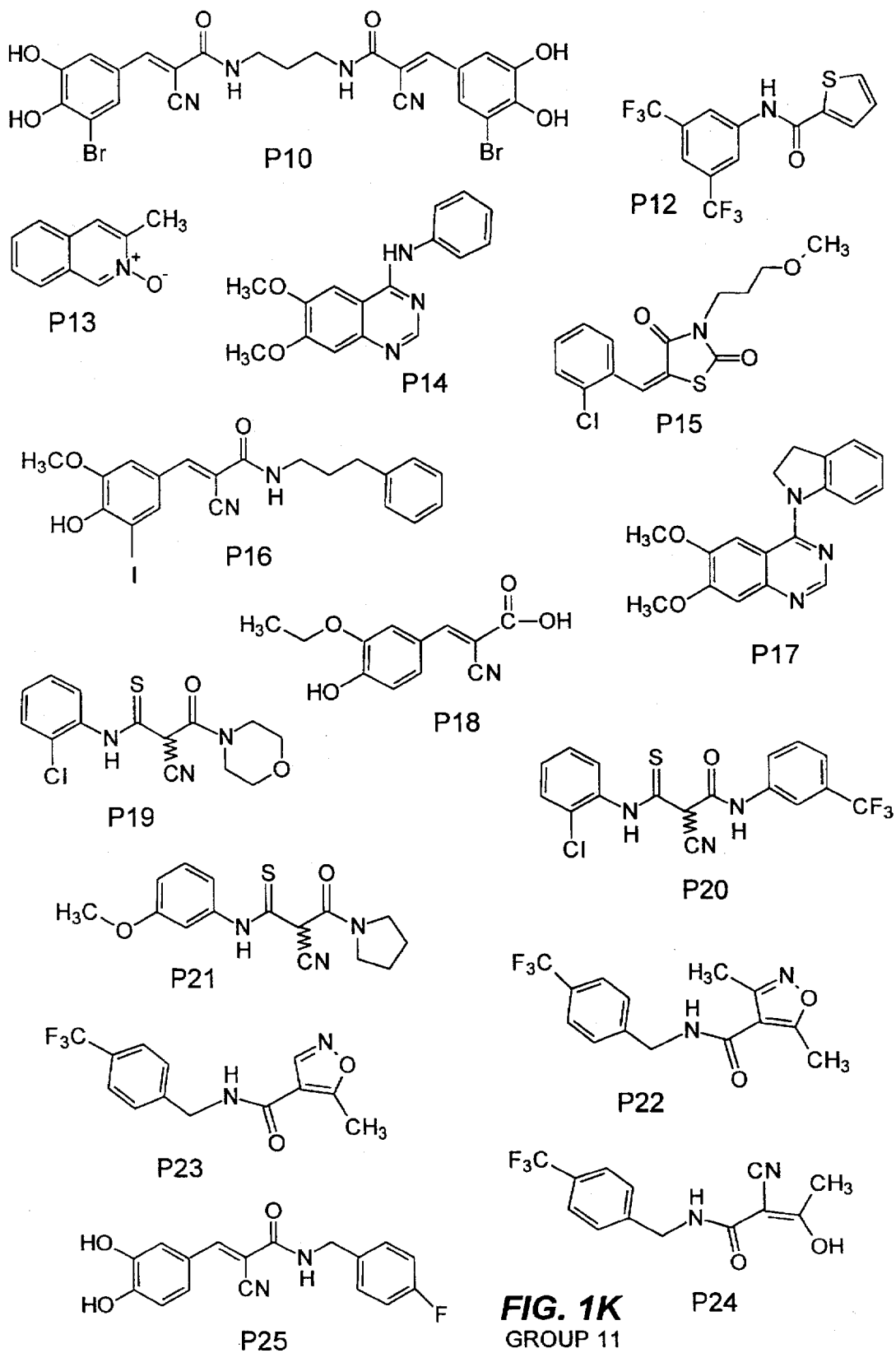

| Compound | $R_{26}$ | $R_{27}$ | $R_{28}$ |
| --- | --- | --- | --- |
| H10 | CH$_3$ | benzyl | 3,4-dihydroxy-phenyl |
| H11 | CH$_3$ | benzyl | 2-hydroxyphenyl |
| H12 | CH$_3$ | benzyl | 3-hydroxyphenyl |
| H13 | CH$_3$ | benzyl | 4-hydroxyphenyl |
| H14 | CH$_3$ | benzyl | 3,4,5-trihydroxy-phenyl | where $R_{29}$ is either hydrogen or halogen, preferably hydrogen; $R_{30}$ is either alkyl, alkenyl, or alkynyl, preferably CH$_3$; $R_{31}$ is aryl, preferably phenyl; and $R_{32}$ is either =O or =S. An example of a group 8 compound is I10, shown in FIG. 1i.

An "alkyl" group refers to a saturated aliphatic hydrocarbon, including straight-chain, branched-chain, and cyclic alkyl groups. Preferably, the alkyl group has 1 to 12 carbons, more preferably from 3 to 9 carbons. The alkyl group may be substituted or unsubstituted. When substituted the substituted groups is preferably, hydroxyl, cyano, alkoxy, =O, =S, NO$_2$ or N(CH$_3$)$_2$, amino, SH, or aryl.

An "alkenyl" group refers to an unsaturated hydrocarbon group containing at least one carbon-carbon double bond, including straight-chain, branched-chain, and cyclic groups. Preferably, the alkenyl group has 1 to 12 carbons, more preferably from 3 to 9 carbons. The alkenyl group may be substituted or unsubstituted. When substituted the substituted groups is preferably, hydroxyl, cyano, alkoxy, =O, =S, NO$_2$ or N(CH$_3$)$_2$, amino, SH, or aryl.

An "alkynyl" group refers to an unsaturated hydrocarbon group containing at least one carbon-carbon triple bond, including straight-chain, branched-chain, and cyclic groups. Preferably, the alkynyl group has 1 to 12 carbons, more preferably from 3 to 9 carbons. The alkynyl group may be substituted or unsubstituted. When substituted the substituted groups is preferably, hydroxyl, cyano, alkoxy, =O, =S, NO$_2$ or N(CH$_3$)$_2$, amino, SH, or aryl.

An "alkoxy" group refers to an "—O-alkyl" group, where "alkyl" is defined as described above.

An "aryl" group refers to an aromatic group which has at least one ring having conjugated pi electron system and includes carbocyclic aryl, heterocyclic aryl and biaryl groups, all of which may be optionally substituted. The preferred substituents of aryl groups are hydroxyl, cyano, alkoxy, alkyl, alkenyl, alkynyl, amino, and aryl groups. Carbocyclic aryl groups are groups wherein the ring atoms on the aromatic ring are carbon atoms. The carbon atoms are optionally substituted. Carbocyclic aryl groups include monocyclic carbocyclic aryl groups and optionally substituted naphthyl groups.

Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted.

A "carbalkoxy" group refers to a COOX group, wherein "X" is an lower alkyl group.

The term "lower" referred to herein in connection with organic radicals or compounds respectively defines such with up to and including 7, preferably up to and including 4, and advantageously one or two carbon atoms. Such groups may be straight chain or branched.

Cell Proliferative Disorders

The described compositions and methods are designed to inhibit cell proliferation diseases by inhibiting PDGF-R activity. As discussed above, proliferative disorders result in unwanted cell proliferation of one or more subset of cells in a multicellular organism resulting in harm to the organism. Inappropriate PDGF activity can stimulate the growth of cell proliferative disorders. Two ways in which inappropriate PDGF or PDGF-R activity can stimulate unwanted cell proliferation of a particular type of cell are by directly stimulating growth of the particular cell, or by increasing vascularization of a particular area, such as tumor tissue, thereby facilitating growth of the tumor.

The use of the present invention is facilitated by first identifying whether the cell proliferation disorder is PDGF-R driven. Once such disorders are identified, patients suffering from such a disorder can be identified by analysis of their symptoms by procedures well known to medical doctors. Such identified patients can then be treated as described herein.

Determination of whether the cell proliferation disorder is PDGF-R driven can be carried out by first determining the level of PDGF-R activity occurring in the cell or in a particular body location. For example, in the case of cancer cells the amount of PDGF-R is determined and compared to non-PDGF-R driven cancers (e.g. A431 cells as described below) and PDGF-R driven cancers (e.g., T98G glioblastoma cells as described below). If the cancer cells have a higher level of PDGF-R activity than non-PDGF-R driven cancers, preferably equal to or greater than PDGF-R driven cancers, then they are candidates for treatment using the described PDGF-R inhibitors.

In the case of cell proliferative disorders arising due to unwanted proliferation of non-cancer cells, the level of PDGF-R activity is compared to that level occurring in the general population (e.g., the average level occurring in the general population of people or animals excluding those people or animals suffering from a cell proliferative disorder). If the unwanted cell proliferation disorder is characterized by a higher PDGF-R level then occurring in the general population then the disorder is a candidate for treatment using the described PDGF-R inhibitors.

Cell proliferative disorders include cancers, blood vessel proliferation disorders, and fibrotic disorders. These disorders are not necessarily independent. For example, fibrotic disorders may be related to, or overlap with, blood vessel disorders. For example, atherosclerosis (which is characterized herein as a blood vessel disorder) results in the abnormal formation of fibrous tissue.

A cancer cell refers to various types of malignant neoplasms, most of which can invade surrounding tissues, and may metastasize to different sites, as defined by Stedman's Medical Dictionary 25th edition (Hensyl ed. 1990). Examples of cancers which may be treated by the present invention include those intra-axial brain cancers, ovarian cancers, colon cancers, prostate cancers, lung cancers, Kaposi's sarcoma and skin cancers, which have inappropriate PDGF-R activity. These types of cancers can be further characterized. For example, intra-axial brain cancers include glioblastoma multiforme, anaplastic astrocytoma, astrocytoma, ependymoma, oligodendroglioma, medulloblastoma, meningioma, sarcoma, hemangioblastoma, and pineal parenchymal.

The formation and spreading of blood vessels, or vasculogenesis and angiogenesis respectively, play important roles in a variety of physiological processes such as embryonic development, wound healing and organ regeneration. They also play a role in cancer development. Blood vessel proliferation disorders refer to angiogenic and vasculogenic disorders generally resulting in abnormal proliferation of blood vessels. Examples of such disorders include restenosis, retinopathies, and atherosclerosis.

The advanced lesions of atherosclerosis result from an excessive inflammatory-proliferative response to an insult to the endothelium and smooth muscle of the artery wall. (Ross R., Nature 362: 801–809 (1993).) Part of the response appears to be mediated by PDGF-BB secretion, and activation of PDGF-R in endothelial and smooth muscle cells. Both cell migration and cell proliferation play a role in the formation of atherosclerotic lesions.

Fibrotic disorders refer to the abnormal formation of extracellular matrix. Examples of fibrotic disorders include hepatic cirrhosis and mesangial cell proliferative disorders.

Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Inappropriate PDGF-R activity can stimulate lipocyte proliferation.

Mesangial cell proliferative disorders refer to disorders brought about by abnormal proliferation of mesangial cells. Mesangial proliferative disorders include various human renal diseases, such as glomerulonephritis, diabetic nephropathy, malignant nephrosclerosis, thrombotic microangiopathy syndromes, transplant rejection, and glomerulopathies. PDGF has been implicated in the maintenance of mesangial cell proliferation. (Floege, J. et al., *Kidney International* 43S: 47–54 (1993).)

As noted above, other such proliferative diseases can be identified by standard techniques, and by determination of the efficacy of action of the compounds described herein.

Ovarian cancer

One aspect of the invention relates to the treatment of ovarian cancer. Epithelial ovarian cancer accounts for nearly 90% of all ovarian tumors and continues to be a highly lethal malignancy. Approximately 19,000 new cases of ovarian cancer are diagnosed in the United States annually, and 12,000 of these women will die from the cancer (Rodriguez et al., in DeVita, Hellman, Rosenberg (eds) *Biologic Therapy of Cancer*, J B Lippincott, 1991).

Treatment for advanced ovarian cancer generally includes cytoreductive surgery followed by combination chemotherapy with alkylating agents such as cisplatin and cyclophosphamide. However, long term survival of advanced ovarian cancer patients is extremely poor, in the range of 10%–20%, principally because of the high incidence of metastatic tumors throughout the peritoneal cavity, and, in some cases, the lymph-nodes. Moreover, chemotherapy with cisplatin carries a potential for renal toxicity and progressive neuropathy.

The invention reveals a pathological relationship between PDGF receptor expression and epithelial ovarian cancer, and provides compositions and methods for inhibiting inappropriate PDGF-R activity in epithelial ovarian cancer cells to inhibit proliferation of the disease. Methods of treating ovarian cancers comprise administering a composition which inhibits inappropriate PDGF-R activity in ovarian carcinoma cells, in supporting stromal cells (i.e., the framework upon which a tumor or metastatic lesion grows, including but not limited to connective tissue and vascular endothelial cells), and/or in associated vascular endothelial cells.

Ovarian cancers susceptible to treatment with the compounds described herein include epithelial ovarian carcinoma, ovarian tumor metastases, and other cells of the ovary which express PDGF receptors. As described below, compositions which inhibit PDGF-R activity also inhibit proliferation of ovarian cancer cells in vitro and inhibit the growth of ovarian tumors in vivo. More specifically, the use of one composition of the invention, A10, results in nearly complete inhibition of ovarian tumor growth in mice xenotransplanted with human ovarian cancer cells, without significant cytotoxicity or mortality, thus providing a dramatic therapeutic effect.

Accordingly, as an example of the method of the invention, A10 is administered to a patient diagnosed with ovarian cancer via any route of administration and in any suitable pharmaceutical carrier which results in bringing A10 in contact with PDGF receptor-positive ovarian cancer cells and/or cells of the surrounding stroma. In view of the localized spread of ovarian cancer throughout the peritoneal cavity, a preferred method of administration, particularly in advanced cases, is by intravenous or intraperitoneal injection of a non-toxic pharmaceutical formulation of A10.

The preparation and use of therapeutically effective compositions for treating ovarian cancers are described in detail in the sections which follow and by way of examples, infra. In addition to the compositions specifically disclosed herein, the invention provides for the identification of other compositions which, because of their inhibitory effect on PDGF activity may be useful for inhibiting the proliferation of ovarian neoplasms. Candidate compositions may be identified by their ability to inhibit PDGF receptor autophosphorylation using any suitable assay, such as in vitro autophosphorylation inhibition ELISA and tyrosine kinase inhibition assays. Candidate compositions may be evaluated for therapeutic efficacy by testing their capacity to inhibit ovarian cancer cell growth and, ideally, by testing inhibition of xenografted tumors in vivo. The procedures described in the examples, infra, or similar procedures, may be employed for conducting such tests.

Glioma

Another aspect of the invention relates to the treatment of primary intra-axial brain tumors of the glioma family, including, but not limited to, astrocytomas and glioblastomas. Glioblastoma multiforme is the most common and most malignant tumor of astrocytic origin in human adults and accounts for more than half of all primary brain tumors (See, for example, *Cecil Textbook of Medicine*, Wyngaarden, Smith, Bennett (eds) WB Saunders, 1992, p. 2220).

Gliomas have the common property of direct invasive involvement of brain tissue, are fundamentally malignant, and are inevitably fatal. Glioblastoma patients have a median survival time of less than one year even when treated aggressively with a combination of surgery, chemotherapy, and radiotherapy. Unfortunately, successful surgical intervention is extremely rare in view of the difficulty or impossibility of defining the microscopic borders of a glioma within normal brain tissue. Similarly, chemotherapy with alkylating agents has met with very little success, and no more than 10% of glioma patients respond significantly. Radiation therapy has demonstrated some value in controlling the growth of gliomas, but often results in substantial neurologic impairment. Therapy with interferon-β, in combination with radiotherapy and chemotherapy, has met with some success (DeVita, Hellman, Rosenberg (eds) *Biologic Therapy of Cancer*, J B Lippincott, 1991).

The invention reveals a pathological relationship between PDGF receptor expression and glioma, and provides compositions and methods for inhibiting PDGF activity in glioma cells to inhibit proliferation of the disease. Methods of treating gliomas comprise administering a composition which inhibits PDGF-R activity expressed in glioma cells and/or in proximate vascular endothelial cells. In particular, most of the compositions specifically disclosed herein are highly active at inhibiting PDGF receptor autophosphorylation in human glioma cells in vitro. Several of these compositions inhibit the growth of cultured glioma cells, and one of these, A10, also inhibits the growth of various glioma explant cultures. Moreover, A10 strongly suppresses the growth of xeno-grafted gliomas in mice; in some animals, tumor growth was inhibited by greater than 95% relative to untreated controls.

Accordingly, as an example of the method of the invention, A10 is administered to a glioma patient via any route of administration and in any suitable pharmaceutical carrier which will result in bringing A10 in contact with PDGF receptor-positive glioma cells, as well as proximate vascular endothelial cells, which typically proliferate in high grade gliomas. Intravenous and intra-arterial routes may be preferred routes of administration. In addition, recentlydeveloped micro-catheter technology may be particularly effective at delivering the compositions of the invention directly to the site of the glioma, thereby achieving immediate localized contact with the cancer and proximate endothelial cells and possibly minimizing potential toxicity associated with more distal intra-arterial delivery.

The preparation and use of therapeutically effective compositions for the treatment of gliomas are described in detail in the sections which follow and by way of examples, infra. In addition to the compositions specifically disclosed herein, the invention provides for the identification of other compositions which, because of their inhibitory effect on PDGF receptor activity, may be useful for inhibiting the proliferation of various intra-axial tumors. Candidate compositions may be identified by their ability to inhibit PDGF receptor activity using any suitable assay, such as in vitro autophosphorylation inhibition ELISA and tyrosine kinase inhibition assays. Candidate compositions may be evaluated for therapeutic efficacy by testing inhibition of glioma cell growth and, ideally, by testing inhibition of xenografted tumors in vivo.

In Vivo Inhibition Of Cell Proliferative Disorders By A10

The present invention describes various compositions which can be used to inhibit PDGF-R activity and thereby inhibit cell proliferation disorders. The use of A10 to inhibit tumor growth in animals demonstrates the ability of these compositions to function in vivo despite various pharmacological considerations which are expected to prevent the composition from exerting its effect. Such in vivo inhibition is illustrated in the examples described below.

A10 is also known as leflunomide, HWA 486, and 5-methylisoxazole-4 carboxylic acid-(4-trifluromethyl)-anilide. Various publications have discussed different possibly uses of A10. According to the abstracts of K emmerer F-J, et al., U.S. Pat. No. 4,284,786 (1981) and K emmerer F-J, et al., U.S. Pat. No. 4,351,841 (1982), A10 "has antirheumatic, antiphlogistic, antipyretic and analgesic action, and can be used for the treatment of multiple sclerosis." According to Talmadge J. E., and Twardzik D. R. *Agents and Actions* 35S: 135-141 (1991), "the hypothesis was suggested that the mechanisms of Leflunomide activity may be the inhibition of a cytokine specific kinase." Robertson S. M. and Lang L. S., European Patent Application 0 413 329 A2 (published 1991) which is concerned with 5-methylisoxazole-4-carboxylic acids that encompass leflunomide, asserts:

The present invention is directed to methods for treating ocular diseases with immune etiology through the use of 5-methyl-isoxazole-4-carboxylic acid anilides and hydroxyethlidene-cyano acetic acid anilide derivatives. In addition the compounds are useful for treating ocular manifestation associated with systemic diseases with immune etiology. The compounds exhibit immunosuppressive, antiinflammatory, and mild antiallergic activity and are useful for the treatment of eye diseases such as uveitis (including rheumatoid nodules), retinitis, allergy (vernal keratocon junctivitis and allergic or giant papillar conjunctivitis) and dry eye (Sjogren's syndrome). Additionally the compounds are useful for prolonging graft survival of corneal or other ocular tissue and are useful as surgical adjuncts in patients which are atopic or immune impaired.

The abstract of Barlett R. R. et al., entitled "Isoxazole-4-Carboxamides and Hydroxyalklidene-Cyanoacetamides, Drugs Containing These Compounds and Use of Such Drugs" PCT/EP90/01800, asserts:

Isoxazole-4-carboxamide derivatives and hydroxyalkylidene-cyanoacetamide derivatives are suitable for the treatment of cancer diseases. These compounds can be prepared by prior art methods. Some of them are new and are suitable, in addition, for the treatment of rheumatic diseases.

Bartlett R. R. et al., *Agents and Actions* 32: 10–21 (1991), asserts that "[l]eflunomide has been shown to be very effective in preventing and curing several autoimmune animal diseases." Barlett also asserts that ..., we could show that tyrosine phosphorylation of the RR-SRC peptide substrate and the autophosphorylation of the epidermal growth factor (EGF) receptor were, dose dependently, inhibited by leflunomide.

Matter et al., *FEBS* 334: 161–164 (Nov. 1993)(not admitted to be prior art) describes the use of the active metabolite of leflunomide to inhibit EGF-dependent cell growth, including A431 cells. Matter also asserts:

Platelet-derived growth factor-dependent tyrosine phosphorylation was also inhibited by A77 1726 in intact cells at concentrations similar to EGF-dependent phosphorylation described in FIG. 3 (data not shown).

Studies on one composition of the invention, A10, described more fully and by way of example infra, establish its potency against brain, lung, prostate, ovarian, skin, and colon cancer cells characterized by inappropriate PDGF-R activity rather than EGF activity. As illustrated in the examples described below A10 selectively inhibits PDGF-R activity, having little if any effect on EGF-receptor or HER$_2$-receptor phosphorylation. In addition, while A10 inhibited growth of tumors characterized by inappropriate PDGF-R activity, A10 did not significantly inhibit the growth of xenotransplanted cells expressing EGF receptor (A431 epidermoid cells). This data is surprising in view of the results described by Bartlett et al., supra, *Agents and Actions* in which leflunomide was shown to inhibit EGF induced EGF receptor autophosphorylation and cell proliferation, and Matter et al., supra, in which the active metabolite of leflunomide inhibited growth of A431 cells.

The present disclosure demonstrates the ability of A10 to inhibit inappropriate PDGF-R activity and unwanted cell proliferation in vivo, such as occurring in cancers characterized by inappropriate PDGF-R activity. As illustrated by the examples described below, A10 can be used to selectively inhibit inappropriate PDGF-R activity A compound is judged to effect phosphorylation if its ability to inhibit phosphorylation of a receptor (e.g., the IC$_{50}$ as described below) is less than its cytotoxic effect (e.g., the LD$_{50}$ as described below). Inhibition of phosphorylation of different receptor such as PDGF-R, EGF-R or HER-2 receptor is dependent on conditions such as drug concentration. By "selectively inhibit" it is meant that a compound can be used at a particular concentration to inhibit phosphorylation of the PDGF-R and have little if any effect on the phosphorylation of the EGF-R and/or HER-2 receptor at the same concentration.

Preferably, the compound, like A10 can inhibit PDGF-R while having little if any effect on EGF-R and/or HER-2 phosphorylation. By "little if any effect" on EGF-R, or HER-2, activity is meant the receptor activity is effected no more than 35%, more preferably, no more than 20%, most preferably no more than 10%.

Tyrosine kinases are important in many biological processes including cell growth, differentiation, aggregation, chemotaxis, cytokine release, and muscle contraction. Many of these events are mediated through different tyrosine kinase receptors. In addition, different tyrosine kinase receptors may be important for a particular biological function in different cell types. By developing selective inhibitors of PDGF-R the possible toxic effect of the compound is decreased.

The compounds described herein vary in their ability to selectively inhibit PDGF-R. For example D14, G12, G13 and G14 inhibit PDGF-R phosphorylation but do not effect EGF or Her-2 phosphorylation, while C10 effects EGF, PDGF, and Her-2 phosphorylation.

In Vivo Inhibition Of Cell Proliferative Disorders By a mutated PDGF-R

Cell proliferative disorders characterized by inappropriate PDGF-R activity can also be inhibited using a mutated PDGF-R. Ueno H., et al., Science 252: 844–252 (1991), describe nucleic acid encoding truncated PDGF-R to inhibit PDGF-R phosphorylation in vitro. According to Ueno:

> When truncated receptors were expressed in excess compared to wild-type receptors, stimulation by PDGF of receptor autophosphorylation, association of phosphatidylinositol-3 kinase with the receptor, and calcium mobilization were blocked.

Ueno did not demonstrate that inhibition of PDGF-R activity by a mutated protein could inhibit unwanted cell proliferation.

Such in vivo inhibition of unwanted cell proliferation is illustrated in the examples described below using nucleic acid encoding the PDGF-R having a stop codon just upstream from the first tyrosine kinase domain. The nucleic acid is used to introduce the truncated protein into a cell. For example, the nucleic acid encoding a truncated PDGF-R is placed into a retroviral vector using standard recombinant DNA techniques. The vector then infects a cell where its nucleic acid is ultimately translated into protein producing a truncated PDGF-R. Other means of introducing the mutated protein into a cell include preparing the mutated protein in vitro and introducing the protein into the cell with a vector, such as a liposome.

Mutant PDGF-R should be constructed to interfere with intermolecular phosphorylation that occurs between dimerized receptor. This can be accomplished by various means such as 1) truncation of the PDGF-R, preferably to eliminate one tyrosine kinase domain, and most preferably to eliminate both tyrosine kinase domains; 2) mutations which inhibit the catalytic ability of the PDGF-R catalytic domain, such as mutation of lysine 602 to arginine which prevents the binding of ATP. Of these methods, mutation of tyrosine residues is preferred and truncation of the receptor is most preferred.

The use of nucleic acid encoding truncated PDGF-R to inhibit tumor growth in animals demonstrates the ability of such truncated receptors to function in vivo despite various pharmacological considerations which would be expected to prevent the composition from exerting its effect. Thus, present disclosure demonstrates that the use of nucleic acid encoding truncated PDGF receptor is not limited to inhibition of PDGF-R in cell culture. Rather nucleic acid encoding PDGF-R can be used to inhibit inappropriate PDGF-R activity in animal cells thereby inhibiting the growth of tumors in animal cells, and having application in other PDGF-R related disorders.

Administration Of Featured Compounds

The compounds of this invention can be administered to a patient alone, or in a pharmaceutical composition comprising the active compound and a carrier or excipient. The compounds can be prepared as pharmaceutical acceptable salts (i.e., non-toxic salts which do not prevent the compound from exerting its effect).

Pharmaceutically acceptable salts can be acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See e.g., supra. PCT/US92/03736). Such salts can derived using acids such as hydrochloric acid, sulfuric acid, phosphoric acid and sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In a another example, the salt is prepared by reacting the free base and acid in an organic solvent.

Carriers or excipient can be used to facilitate administration of the compound, for example, to increase the solubility of the compound. Examples of carriers and excipient include calcium carbonate, calcium phosphate, various sugars or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmuccosally.

Several of the featured compounds, such as A10 and B11, are hydrophobic and thus not very soluble in water. Effective doses of A10 can be obtained by using A10 in combination with PBTE:D5W. PBTE consists of a solution of 3% w/v benzyl alcohol, 8% w/v polysorbate 80, and 65% w/v polyethylene glycol (MW=300 daltons) in absolute ethanol. PBTE:D5W consists of PBTE diluted 1:1 in a solution of 5% dextrose in water. The solubility of A10 in PBTE is about 60 mg/ml, and the solubility of A10 in PBTE:D5W is about 5 mg/ml. The solubility of the other compounds described herein can be obtained using standard techniques. In addition, the active drug itself (e.g., B11) may be administered in an oral formulation.

Another way of overcoming the hydrophobicity problem includes the use of frequent small daily doses rather than a few large daily doses. For example, the composition can be administered at short time intervals, preferably the composition can be administered using a pump to control the time interval or achieve continuously administration. Suitable pumps are commercially available (e.g., the ALZET® pump sold by Alza corporation, and the BARD ambulatory PCA pump sold by Bard MedSystems).

Alternatively, prodrugs having increased solubility can be used. Prodrugs can break down into the active drug under physiological conditions. For example, Patterson et al., *J. Med. Chem.* 35: 507–510 (1992), describes A12 (3-carboxy-5-methyl-N-[4(triflouromethyl)phenyl]-4-isoxazole-carboxamide) which, like A10, can act as a prodrug for B11.

The proper dosage depends on various factors such as the type of disease being treated, the particular composition being used, and the size and physiological condition of the patient. For the treatment of cancers the expected daily dose of A10 is between 1 to 2000 mg/day, preferably 1 to 250 mg/day, and most preferably 10 to 150 mg/day. Drugs can be delivered less frequently provided plasma levels of the active moiety are sufficient to maintain therapeutic effectiveness.

A factor which can influence the drug dose is body weight. Drugs should be administered at doses ranging from 0.02 to 25 mg/kg/day, preferably 0.02 to 15 mg/kg/day, most preferably 0.2 to 15 mg/kg/day. Alternatively, drugs can be administered at 0.5 to 1200 mg/m$^2$/day, preferably 0.5 to 150 mg/m$^2$/day, most preferably 5 to 100 mg/m$^2$/day. The average plasma level should be 50 to 5000 µg/ml, preferably 50 to 1000 µg/ml, and most preferably 100 to 500 µg/ml. Plasma levels may be reduced if pharmacological effective concentrations of the drug are achieved at the site of interest.

Administration Of Mutated PDGF-R

The PDGF-R mutants can be administered as protein, or nucleic acid expressing the protein, using standard techniques some of which are discussed below. Delivery vehicles include liposomes and other pharmaceutical compositions. Nucleic acid encoding a mutated PDGF-R can also be introduced into a cell using standard techniques such as a retroviral vector, iontophoresis, electroporation, ion paired molecules, or covalently attached adducts. In those cases where the technique is carried out ex vivo the cell is then put into a patient. Administration of protein is facilitated using a carrier or excipient as described above.

The specific delivery route of any selected agent depends on the use of the agent (such considerations are also applicable for the administration of the featured compounds). Generally, a specific delivery program for each agent focuses on agent uptake with regard to intracellular localization, followed by demonstration of efficacy. Alternatively, delivery to these same cells in an organ or tissue of an animal can be pursued. Uptake studies include uptake assays to evaluate, e.g., cellular nucleic acid or protein uptake, regardless of the delivery vehicle or strategy. Such assays also determine the intracellular localization of the agent following uptake, ultimately establishing the requirements for maintenance of steady-state concentrations within the cellular compartment containing the target sequence (nucleus and/or cytoplasm). Efficacy and cytotoxicity can then be tested. Toxicity not only includes cell viability but also cell function. Generally, the dosages of the mutated protein and nucleic acid is as described above for the featured compounds.

Drug delivery vehicles are effective for both systemic and topical administration. They can be designed to serve as a slow release reservoir, or to deliver their contents directly to the target cell. An advantage of using direct delivery drug vehicles is that multiple molecules are delivered per uptake. Such vehicles increase the circulation half-life of drugs which would otherwise be rapidly cleared from the blood stream. Some examples of such specialized drug delivery vehicles falling into this category are liposomes, hydrogels, cyclodextrins, biodegradable nanocapsules, and bioadhesive microspheres. Pumps can also be used for this purpose.

From this category of delivery systems, liposomes are preferred. Liposomes increase intracellular stability, increase uptake efficiency and improve biological activity. Liposomes are hollow spherical vesicles composed of lipids arranged in a similar fashion as those lipids making up the cell membrane. They have an internal aqueous space for entrapping water soluble compounds and range in size from 0.05 to several microns in diameter. Antibodies can be attached to liposomes to target particular cells.

Topical administration of PDGF-R mutants and the featured compounds is advantageous since it allows localized concentration at the site of administration with minimal systemic adsorption. This simplifies the delivery strategy of the agent to the disease site and reduces the extent of toxicological characterization. Furthermore, the amount of material applied is far less than that required for other administration routes. Effective delivery requires the protein or nucleic acid to enter the cell membrane or the cytoplasm of cells characterized by inappropriate PDGF-R activity.

Agents may also be systemically administered. Systemic absorption refers to the accumulation of drugs in the blood stream followed by distribution throughout the entire body. Administration routes which lead to systemic absorption include: intravenous, subcutaneous, intraperitoneal, intranasal, intrathecal and ophthalmic. Each of these administration routes expose the drug to an accessible diseased tissue. Subcutaneous administration drains into a localized lymph node which proceeds through the lymphatic network into the circulation. The rate of entry into the circulation has been shown to be a function of molecular weight or size.

EXAMPLES

Examples are provided below to illustrate different aspects and embodiments of the present invention. These examples are not intended in any way to limit the disclosed invention. Rather, they illustrate methodology by which drugs having the disclosed formula can be readily identified by routine procedure to ensure that they have the desired activity. That is, compounds within the formula claimed herein can be screened to determine those with the most appropriate activity prior to administration to an animal or human. Other compounds can also be screened to determine suitability for use in methods of this invention.

Cell Growth

All cell culture media, glutamine, and fetal bovine serum were purchased from Gibco. Rat C6 glioma cells (ATCC #CCL 107) were maintained in Ham's F10 supplemented with 5% fetal bovine serum (FBS) and 2 mM glutamine. The human glioblastoma cell line T98G (ATCC #CRL 1690) was cultured in MEM with 10% FBS, 2 mM glutamine, 1 mM sodium pyruvate and non-essential amino acids. U1242MG cells were cultured in MEM with 10% FBS, 1 mM sodium pyruvate, 2 mM glutamine and 0.1 mM non-essential amino acids. A431 cells (obtained from the ATCC) were cultured in DMEM+10% FBS+2 mM glutamine. SKOV-3 cells were cultured in DMEM +10% FBS+2 mM glutamine. Parental and xenograft-derived lines were cultured similarly. All cell lines were routinely subcultured twice a week and were negative for mycoplasma as determined by the Mycotect method (Gibco).

Example 1

Inhibition of PDGF-R autophosphorylation by A10

This example illustrates the ability of A10 to inhibit PDGF-R autophosphorylation of rat C6 glioma cells. Rat C6 glioma cells ($5 \times 10^5$) were plated in MCDB105 medium containing 5% FCS in a 6-well plate and incubated for 24 hours at 37° C. The cells were then placed in media with 1% FCS for another 24 hours. The cells were treated with A10 at 50, 100, or 200 µM for one hour at 37° C. The cells were then treated with 20 ng/ml of PDGF-BB for 10 minutes at 37° C. The cells were lysed in 50 mM Tris-HCl (pH 7.4) containing 2 mM EDTA, 10% glycerol, 1% NP-40, 1 mM Na$^+$orthovanadate, 10 mM pyrophosphate, 1 mM PMSF, 10 µg/ml aprotinin and 10 µg/ml leupeptin.

Proteins were then separated by SDS-polyacrylamide gel electrophoresis (PAGE). Proteins containing phosphorylated tyrosine were identified by western blotting with an anti-phosphotyrosine antibody. The level of phosphorylated tyrosine was determined by quantitating the amount of bound anti-phosphotyrosine. Quantitation was carried out by peak area integration using a Molecular Dynamics Computing Densitometer (Model 300S), and Image Quant v3.0 software (Molecule Dynamics). Data were expressed as relative peak intensity (phosphorylation of a receptor divided by the total amount of phosphorylated tyrosine).

PDGF-BB stimulated autophosphorylation of the PDGF-R, while A10 inhibited such stimulation. Increasing concentrations of A10 resulted in reduced PDGF stimulated receptor phosphorylation. A10 at a concentration of 200 µM reduced PDGF-R phosphorylation below that occurring in the absence of PDGF-BB stimulation.

Example 2

Selective inhibition of PDGF-R autophosphorylation by A10

A10 inhibits autophosphorylation of the PDGF-R in human T98G glioblastoma cells, while having little if any effect on autophosphorylation of the EGF receptor. T98G cells were plated in MCDB105 medium containing 2% FBS and incubated for 24 hours at 37° C. The media was aspirated and then replaced with MCDB105 and the cells were treated for one hour with 200, 500 or 1,000 µM A10. The cells were then treated with ligand for 10 minutes (20 ng/ml PDGF-BB or 50 ng/ml EGF). The cells were lysed and the level of phosphorylated receptor was quantitated as described in Example 1.

Cells were treated with different concentrations of A10 (0, 200, 500 and 1000 µM) and in the presence or absence of ligand. The ligand for PDGF-R phosphorylation was 20 ng/ml PDGF-BB. The ligand for EGF-R phosphorylation was 50 ng/ml EGF. A10 inhibited autophosphorylation of PDGF-R by PDGF, but had little if any effect on the ability of EGF to stimulate autophosphorylation of EGF-R.

Example 3

Inhibition of PDGF-R phosphorylation By various compounds.

This example illustrates the ability of various compounds to inhibit PDGF-stimulated receptor phosphorylation. U1242 MG cells were plated in 96-well plates at a concentration of 5×10⁴ cells/well in cultured media containing 0.5% FBS. The cells were incubated for 24 hours. The cells were then treated with a particular compound for 2 hours followed by the addition of 100 ng/ml PDGF-BB and incubation for 10 minutes.

Cells were lysed in 0.2M Hepes, 0.15M NaCl, 10% V/V glycerol, 0.04% Triton X-100, 5 mM EDTA, 5 mM Na⁺vanadate and 2 mM Na⁺ pyrophosphate. Cell lysates were then added to an ELISA plate coated with an anti-PDGF receptor antibody (Genzyme). ELISA plates were coated at 0.5 µg of antibody/well in 150 µl of PBS for 18 hours at 4° C. prior to the addition of the lysate.

The lysate was incubated in the coated plates for 1 hour and then washed four times in TBST (35 mM Tris-HCl pH 7.0, 0.15M NaCl, 0.1% Triton X-100). Anti-phosphotyrosine antibody (100 µl in PBS) was added and the mixture was incubated for 30 minutes at room temperature. The wells were then washed four times in TBST, a secondary antibody conjugated to POD (TAGO) was added to each well, and the treated well were incubated for 30 minutes at room temperature. The wells were then washed four times in TBST, ABTS/H$_2$O$_2$ solution was added to each well and the wells were incubated for two minutes. Absorbance was then measured at 410 nm.

The cytotoxicity of each drug was also determined. The cells were plated as described above. Following incubation with drug, cell survival was measured by an MTT assay as described by Mossman *J. Immunol. Methods* 65: 55–63 (1983), or by measuring the amount of LDH released (Korzeniewski and Callewaert, *J. Immunol. Methods* 64:

313 (1983); Decker and Lohmann-Matthes, *J. Immunol. Methods* 115: 61 (1988).

The results are shown in Table IX. IC$_{50}$ valves (i.e., the dose required to achieve 50% inhibition) were determined using the ELISA screening assay. LD$_{50}$ values (i.e., the dosage which results in 50% toxicity) were determined using an MTT or LDH assay.

IC$_{50}$ values for inhibiting PDGF-stimulated receptor phosphorylation in U1242 cells ranged from 0.4 to >500 µM. As seen in Table IX most of the compounds tested inhibited PDGF-stimulated receptor phosphorylation. In all cases inhibition of receptor phosphorylation was not due to non-specific effects on cell viability as shown by the higher LD$_{50}$. Thus, these drugs are good candidates for compounds which can be used to treat cell proliferative diseases by inhibiting PDGF-R activity. G13 and G14 had the lowest IC$_{50}$ but had a LD$_{50}$ less than A10. Generally, the preferred compounds are those having the highest therapeutic index (LD$_{50}$/IC$_{50}$), which is a measure of the safety index.

TABLE IX

| ANALOG ID | ELISA P-TYR U1242 IC50(µM) | CYTOXICITY LDH U1242 LD50(µM) | CYTOXICITY MTT U1242 LD50(µM) |
|---|---|---|---|
| A10 | 65 | >500 | 700 |
| B10 | 180 | | |
| B12 | 100 | >500 | >1351 |
| B13 | 180 | | |
| B14 | 180 | | |
| B15 | 120 | | 200 |
| B16 | 35 | | 50 |
| B17 | 125 | >1000 | >500 |
| B18 | 160 | | |
| B19 | 100 | | |
| C10 | 25 | | >500 |
| C11 | 70 | >500 | >500 |
| D11 | 8 | >441 | 90 |
| D12 | 60 | >386 | >390 |
| D13 | 30 | >500 | >500 |
| D14 | 20 | >100 | >500 |
| D15 | 20 | 400 | 80 |
| D16 | 50 | >168 | >167 |
| D17 | >100 | | |
| E10 | 45 | | |
| E11 | 90 | | |
| E12 | 180 | | |
| E13 | >100 | | |
| E14 | 100 | | |
| E15 | 5 | | >100 |
| E16 | 125 | | |
| F10 | 45 | | |
| F11 | 100 | | |
| F12 | 70 | | |
| G10 | 10 | >485 | >490 |
| G11 | 15 | 90 | 145 |
| G12 | 10 | >333 | >333 |
| G13 | 0.4 | >100 | 100 |
| G14 | 0.8 | >100 | >500 |
| G15 | 100 | | |
| G16 | 35 | | >100 |
| G17 | 100 | | |
| G18 | 10 | >100 | |
| G19 | 90 | | |
| G20 | >100 | | |
| G21 | 6 | >100 | |
| G22 | 1 | >100 | |
| H12 | 30 | | |
| I10 | 90 | >317 | >320 |

Example 4

Inhibition of PDGF-R stimulated DNA synthesis.

This example illustrates the ability of A10 to inhibit PDGF-BB stimulated DNA synthesis in rat C6 glioma cells or human T98G cells. Cells were cultured as described above under the section "cell growth". The assay conditions were essentially those described by Pollack et al., *J. Neurosurg.* 73: 106–112 (1990) with some modifications.

Cells (rat C6 or human T98G) in log phase growth were transferred to 96-well dishes at $2\times10^4$ cells in 200 µl MCDB 105 medium containing 2% FBS. After an overnight attachment period the media was changed to serum free assay media (MCDB 105 with 5 µg/ml insulin) and the cells were incubated for 18–24 hours.

DNA synthesis studies were initiated by adding 50 ng/ml of PDGF-BB alone or in combination with various concentrations of A10. The effect on basal $^3$H-thymidine incorporation was determined in the absence of PDGF. The plates were incubated at 37° C. for approximately 18 hours. $^3$H-thymidine (Amersham, 5 Ci/mmol) was added to each well to yield a final concentration of 5 µCi/ml, the plates were returned to the 37° C. incubator, after 4 hours the medium was removed and the plates were put on ice. Each well was then washed twice with 200 µl ice-cold PBS. Radioactivity incorporated into DNA was separated from unincorporated 3H-thymidine by precipitation with 100 µl ice-cold TCA for 10 minutes. After two washes with ice-cold TCA, the precipitate was solubilized (1% SDS in 100 µl 20 mM Tris-base) and transferred to liquid scintillation counting vials. Six ml of cocktail (Ready Safe, Beckman) was added and radioactivity quantified in a Beckman liquid scintillation counter model LS6000 SC. AD decreased PDGF-stimulated DNA synthesis in both types of cells, however a greater effect was seen in human T98G glioblastoma cells than rat C6 glioma cells.

Example 5

Inhibition of primary tumor

This example illustrates the ability of A10 to inhibit primary tumors isolated from humans. Primary human glioblastoma cells were resected from six patients and treated with A10. The effect of A10 was determined by measuring $^3$H-thymidine uptake, and expression of PDGF-R using tissue blocks.

As the concentration of A10 increased (from O to 400 µM) tumor cell growth decreased. The $IC_{50}$ values ranged from 39 µM to 198 µM, depending upon the patient. A positive correlation between inhibition of tumor growth by A10 and PDGF-R expression was observed.

Example 6

In vivo inhibition of tumor growth by A10 and B11

This example summarizes several experiments illustrating the ability of A10 to inhibit A431 epidermoid cells, rat C6 glioma cells, human SKOV-3(T) ovarian tumor cells, and human glioma cell in vivo, and of B11 to inhibit rat C6 glimoa cells in vivo. PDGF may stimulate the growth of tumors directly by stimulating the proliferation of PDGF responsive tumor cells or indirectly by increasing the vasculogenesis of the tumor tissue.

C6 and SKOV-3(T) cells were grown in culture, as described in "cell growth" above, and implanted into the hind flank of a female Balb/c nu/nu mouse at $3\times10^6$ cells (for C6 experiments), or $1\times10^7$ cells (for SKOV-3 experiments) in 100 µl of PBS on Day 0. U87MG, U118MG or U373MG human glioblastoma cells (obtained from the ATCC) were also implanted into athymic mice. Mice implanted with tumors, and non-implanted mice were administered A10 or B11 via intraperitoneal injection in a volume of 50 µl of DMSO, 100 µl PBTE:D5W, or 100 µl PBTE beginning on Day 1 or as otherwise indicated. Tumors were measured using venier calipers and tumor volume was calculated as a product of tumor length, width, and height.

In one set of experiments mice implanted with A431, rat C6 glioma cells, SKOV-3(T) ovarian tumor cells and treated with 15 mg/kg/day of A10 (DMSO). Tumor growth progressed logarithmically in untreated, and DMSO controls. In contrast, tumor growth progressed only slightly (e.g., greater than 90% inhibition in tumor growth after 20 days compared with control) in A10 treated animals implanted with rat C6 glioma cells or SKOV-3(T) ovarian tumor cells. A10 had little (i.e. no more than 25%) effect on A431 tumor growth. Tumor growth of mice implanted with rat C6 glioma cells was inhibited with 15 mg/kg/day of B11 (DMSO) to the extent as implanted mice treated with 15 mg/kg/day of A10 (DMSO).

In another set of experiments mice implanted with C6 glioma sets were treated with A10. Table X summarizes the ability of A10 to inhibit rat C6 glioma cells in athymic mice using different treatment regimens. The percent inhibition refers to size of the tumor from A10 treated animals, divided by the size of the tumor from vehicle control treated animals. The different treatment regimens resulted in inhibition of 51% to greater than 95%.

TABLE X

A10 Dosing Regimen Studies

| Dose | Regimen | % Inhibition |
| --- | --- | --- |
| 20 mg/kg (PBTE:D5W) | daily | >95% |
| 20 mg/kg (DMSO) | 2 days | 77% |
| 20 mg/kg (DMSO) | 4 days | 60% |
| 30 mg/kg (DMSO) | 2 days | 91% |
| 30 mg/kg (DMSO) | 3 days | 87% |
| 40 mg/kg (PBTE) | 2 days | >95% |
| 60 mg/kg (PBTE) | weekly | 51% |
| 100 mg/kg (PBTE) | weekly | 63% |

Table XI presents data illustrating the ability of A10 to inhibit glioblastoma cells in vivo.

TABLE XI

| Cell Line | Dose (mg/kg) | % Inhibition |
| --- | --- | --- |
| U87 | 5 | 52 |
|  | 10 | 58 |
|  | 15 | 66 |
|  | 20 | 92 |
| U118 | 15 | 57 |
| U373 | 15 | 54 |
| SF763T | 20 | 89 |
| SF767T | 20 | 70 |

The percent inhibition refers to tumor size in treated animals versus tumor size in untreated animals.

Table XII compares the efficacy of different A10 formulations in vivo. PBTE, PBTE:D5W and DMSO formulations showed equivalent in vivo inhibition of tumor growth.

TABLE XII

Efficacy vs. Formulation

| Dose | Formulation | % Inhibition |
| --- | --- | --- |
| 15 mg/kg/day | DMSO | 90% |
| 20 mg/kg/day | DMSO | 95% |
| 15 mg/kg/day | PBTE | 92% |
| 20 mg/kg/day | PBTE | >95% |
| 40 mg/kg/2 days | PBTE | >95% |
| 20 mg/kg | PBTE:D5W | >95% |

The effects of A10 on animal mortality, using DMSO, PBTE, or PBTE:D5W formulations is presented in Table XIII. PBTE:D5W formulations significantly reduced the mortality rate compared to DMSO formulations, and PBTE formulations.

TABLE XIII

Effects of A10 on Mortality

| Dose | Treatments | Mortality | n |
| --- | --- | --- | --- |
| 20 mg/kg/day (DMSO) | 21 | 54% | 26 |
| 20 mg/kg/day (PBTE:D5W) | 27–100 | 0% | 80 |
| 25 mg/kg/day (PBTE:D5W) | 67 | 0% | 8 |
| 20 mg/kg/day (PBTE) | 20–48 | 8% | 12 |
| 30 mg/kg/day (PBTE) | 48 | 50% | 4 |
| 40 mg/kg/day (PBTE) | 48 | 75% | 4 |

Many cancer therapeutics are cytotoxic in nature and have profound effects on blood cells resulting in cytopenia. The effects of A10 on the number of red blood cells, white blood cells, and the percent of lymphocytes versus polymorphonuclear cells were examined.

A10 at 15 mg/kg/day, did not appear effect blood differentials over a 21 day period for drug delivered in DMSO, PBTE or PBTE:D5W (1:1). Drug delivered in PBTE:D5W at 20 or 25 mg/kg/day did not affect the number of RBCs, WBCs or percent lymphocytes:neutrophils. However, drug delivered in PBTE alone at 30 mg/kg/day showed a slight decrease in WBCs after 2–3 weeks of treatment. Animals given 40 mg/kg/day showed both anemia and leukopenia after several weeks of treatment when given A10 in PBTE alone. No effects on blood cell were observed when A10 was administered in PBTE:D5W even after 100 days of treatment.

These pharmacology and toxicology studies illustrate that A10 can be administered to animals under conditions having little if any adverse effect on the animal, particularly when PBTE:D5W formulations are used. Other suitable formulations can be obtained by one skilled in the art using this application as a guide.

Example 7

Inhibition of cancer characterized by inappropriate PDGF-R activity

This example illustrates the ability of A10 to inhibit cancers characterized by inappropriate PDGF-R activity while having little or no effect on tumors not characterized by PDGF-R activity. As seen in Table XIV growth inhibition is strongest on cells expressing high levels of PDGF-R, establishing a clear link between receptor activity and cancer cell proliferation.

TABLE XIV

RECEPTOR EXPRESSION vs. GROWTH INHIBITION

| Cell Line | PDGF-R Expression | SRB | SAA | In Vivo |
| --- | --- | --- | --- | --- |
| C6 | ++ | 0.3 | 0.4 | 95% |
| SF767 | − | 100 | ND | 18% |
| SF767T | ++ | 3 | 0.5–2 | 70% |
| SF763 | − | >100 | ND | 35% |
| SF763T | ++ | ND | ND | 89% |
| SKOV-3 | − | >100 | 6.3 | ND |
| SKOV-3T | ++ | 50 | 0.3 | 95% |

PDGF-R expression was measured qualitatively using a western blot. SRB assays assessed cell growth by determining total cellular protein using sulforhodamine-B (Skehan, T et al., *J. Natl. Cancer Inst.* 82: 1107–1112 (1990). Soft agar assays (SAA) were carried out by seeding cells at colony density in a semi-solid agar medium onto a base layer of agar after two to three weeks the size and number of colonies were quantitated with an automated Omincon 3800™ tumor colony counter. SRB and SAA values are expressed as IC50 values in µM. In vivo inhibition was determined in xenografted athymic mice.

Example 8

In vivo inhibition of PC-3 prostate cell line and A375 melanoma cells line

This example illustrates the ability of A10 to inhibit PC-3 prostate cell line and A375 melanoma cells line. SCID mice containing PC-3 prostate cell line were treated with A10 starting 15 days after tumor transplant. The weekly treatment comprised 12 mg/kg/day of A10 (PBTE:D5W) for five days and two days of no treatment. The mice were treated for three week. Mice containing A375 melanoma were treated in the same way except 15 mg/kg/day of A10 was used and treatment began 9 days after tumor implant.

In both cases, tumor growth was inhibited by A10. PC-3 tumor growth was inhibited about 50% after three weeks. A375 melanoma growth was inhibited about 40% after three weeks. Thus, this example further illustrates the utility of A10 to inhibit tumor growth by showing its ability to inhibit tumor which have been growing in a host prior to treatment (Cf. Example 7 where treatment of tumor began one day after transplant).

Example 9

In vivo inhibition of tumor by a mutated PDGF-R receptor

This example illustrates the use of nucleic encoding a truncated PDGF-β receptor to inhibit in vivo tumor growth. C6 rat glioma cells were infected with retroviruses carrying a mutant gene for the human PDGF-β receptor. Seven G418-selected clones were screened for expression of the truncated receptor by Western blotting with an antibody that recognizes the extracellular domain of the human receptor but does not cross-react with the wild type rat receptor. Two clones, HiMut.1 and HiMut.2, express high levels of a protein with the predicted molecular weight for the receptor lacking most of the intracellular region. Several clones expressed low levels of the truncated receptor; LoMut.1 was chosen for further experiments. Himut.1 expressed PDGF-R 8.3 fold higher than LoMut.1. Himut.2 expressed PDGF-R 9.4 fold higher than LoMut.1. The isolation and characterization of the clones containing the mutant receptors were carried out as described below. p Cell culture. All culture media, fetal bovine serum (FBS) and chemicals were purchased from Gibco BRL. C6 rat glioma cells were grown in Ham's/F-10 medium supplemented with 5% fetal bovine serum and 2 mM glutamine. COS cells were cultured in 10% fetal bovine serum and 2 mM glutamine in Dulbecco's Modified Eagle's medium (DMEM).

Expression of mutant PDGF-β receptor. A stop codon was introduced by site-directed mutagenesis into the gene for the human PDGF-β receptor directly upstream from the first tyrosine kinase domain. The mutant gene was cloned into a vector under the control of the murine sarcoma virus long terminal repeat (Muller, A. J., et al., *Mol. Cell. Biol.* 11: 1785-1792, 1991). Four µg each of this vector and a vector containing the genes required for retroviral virus packaging (Muller, supra) were cotransfected into COS cells ($2 \times 10^5$ cells/60 mm plate) by calcium phosphate precipitation (Chen, C. A., and H. Okayama, *BioTech.* 6: 632-638, 1988). The cells were washed with PBS and refed the following day and conditioned media collected on days 4-6 after transfection. C6 cells ($10^5$ cells/60 mmplate) were infected with dilutions of the conditioned media containing 6 µg/ml Polybrene (Sigma). Two days later, the cells were put into selection with 800 µg/ml G418 (Gibco) and colonies picked when distinguishable. The vector control cells were prepared by the same method but with a vector lacking a gene under the LTR.

Co-immunoprecipitation of wild type and truncated receptors. Vector control cells and cells expressing high levels of the mutant PDGF-β receptor (HiMut.1) were each seeded with $3 \times 10^5$ cells/well on 6-well plates. The following day, the media was changed for 0.5 ml 3% FBS in -cys -met DMEM (ICN) containing 100 µCi/ml Tran$^{35}$S-label (ICN). The cells were incubated at 37° C. for 16 hrs. They were washed twice with binding buffer (0.1% BSA, 10 µg/ml CaCl$_2$.2H$_2$O, 10 µg/ml MgSO$_4$.7H$_2$O, 10 µg/ml aprotinin and 0.2 µM PMSF in PBS), and 0.5 ml binding buffer or 0.5 ml 20 ng/ml PDGF-BB (Collaborative Research Inc.) in binding buffer was added to each well. The cells were incubated at 4° C. for 4 hrs, washed twice with PBS and lysed with 0.5 ml 1% Triton X-100 in HNTG (20 mM HEPES (pH 7.5), 150 mM NaCl, Triton X-100, 10% glycerol, 10 µg/ml each of aprotonin, leupeptin and pepstatin, and 0.2 µM PMSF). PDGF-BB was included in the lysis buffer of cells that had been treated with PDGF. The lysates were spun at 100,000 xg for 30 min at 4° C. The supernatants were transferred to new tubes and precleared with Protein A-agarose (Vector Laboratories). SDS was added to a final concentration of 0.1% to 2 PDGF-treated samples for each cell line. Duplicate samples were immunoprecipitated with either an antibody that recognizes the C-terminus of the wild type rat receptor (UBI anti-PDGF-β receptor) or the human mutant receptor (Genzyme anti-PDGF-β receptor). Rabbit anti-mouse IgG was used as a secondary antibody for the samples incubated with the Genzyme anti-receptor. The complexes were precipitated with Protein A-agarose and washed 5 times with 0.1% Triton X-100 in HNTG. The proteins were separated by SDS-polyacrylamide gel electrophoresis on 7.5% gels under reducing conditions. The gels were fixed, treated with Amplify (Amersham) and exposed to X-ray film for 3 days.

Western blotting. Each cell line was plated in multiple wells at $5 \times 10^5$ cells/well on 6-well plates. The following day they were fed with 1% FBS in MCDB 105 (UCSF Cell Culture Facility) and incubated for 24 hrs in a 0% CO$_2$ environment. PDGF-AA or -BB (Collaborative Research Inc.) was added to one well of each clone to the desired final concentration. After incubating for 7 min at room temperature, the cells were washed with PBS and lysed with 50mM Tris-HCl (pH 7.4), 1% nonidet P-40, 10% glycerol, 2 mM EDTA, 10 mM sodium pyrophosphate, 10 µg/ml each aprotinin and leupeptin, 1 mM PMSF and 1 mM sodium orthovanadate. Equal volumes of each lysate were run on multiple 7.5% SDS polyacrylamide gels and transferred to nitrocellulose (Schleicher & Schuell). The membranes were blocked with 5% instant nonfat milk in Tris-buffered saline/ 0.05% Tween-20 (TBS-T). Duplicate membranes were incubated with either polyclonal anti-phosphotyrosine 1:3000 or anti-PDGF-β receptor (UBI) 1:1000 in blocking buffer. The secondary antibody was horseradish peroxidase-conjugated goat anti-rabbit IgG (Sigma) 1:1000. To detect the truncated receptor, a monoclonal antibody against the extracellular domain of the human PDGF-β receptor (Genzyme) diluted 1:500 was utilized. The secondary antibody used was peroxidase-conjugated rabbit anti-mouse IgG (ICN) 1:1000. ECL (Amersham) was used for detection on all blots. Relative band areas were determined with a Molecular Devices Computing Densitometer. Basal levels of phosphorylation were subtracted from each point.

Adherent growth of cell lines. To determine growth densities, each cell line was seeded with $10^4$ cells/well on 5 24-well plates with triplicate samples in 1% or 5% FBS in Ham's/F-10 medium. The media was changed every 3 days. Every 2 days, the cells on one plate were trypsinized and counted on a Coulter counter. To determine cloning efficiencies, 100 cells of each cell line were plated on three 10 cm plates in 1% or 5% FBS in Ham's/F-10 medium. The media was changed every 3 days for about 12 days. The colonies were fixed, stained with methylene blue and scored.

Anchorage-independent growth of cell lines (soft agar assay). A base layer was made in 35 mm plates with 0.8% SeaPlaque agarose (FMC BioProducts), 1% FBS 2 mM glutamine, 1 mM sodium pyruvate, 10 mM HEPES and nonessential amino acids. Cells were suspended in 0.4% agarose containing the other ingredients listed above and the desired concentration of PDGF-BB (Collaborative Research Labs). The suspension was plated on the base layer with 3000 cells/plate. They were incubated for 2 weeks in a humidified chamber with 5% CO$_2$. Colonies were scored visually or with an automated Omincon 3800™ tumor colony counter.

Growth of cell lines in nude mice. Cells were expanded in roller bottles, trypsinized and resuspended in PBS. They were counted and the volume adjusted to $3 \times 10^7$ cells/mi. For each cell line, 4 to 8 athymic nude mice (Simonsen Labs) were injected subcutaneously with 100 µl ($3 \times 10^6$ cells). Tumor volumes were measured with calipers twice a week for 18 to 21 days.

Immunohistochemical staining of tumor sections. Tumors were resected from the mice and frozen in OCT (Miles Lab). Five µm thick sections were cut and fixed with acetone. The sections were blocked with 10% normal goat serum prior to incubation with 20 µg/ml biotinylated-anti-human PDGF-β receptor (Genzyme antibody, biotinylated by Molecular Probes). Peroxidase-conjugated streptavidin (Caltag) 1:100 and diaminobenzidine (Sigma) with H$_2$O$_2$ were used for detection. For a negative control, a biotinylated monoclonal antibody to an unrelated protein was used at the same protein concentration as the anti-PDGF-β receptor. The counter stain was Harris hematoxylin (Anatech).

Using the retroviral expression system described above, a truncated PDGF-β receptor was introduced into rat C6 glioma cells. In G418-resistant clones expressing the mutant receptor, PDGF-BB-induced tyrosine phosphorylation of the wild type receptor was significantly reduced. Furthermore, these cells grew to lower density and formed smaller colonies in culture and in soft agar than the parental C6 cells.

Cells expressing the truncated receptor were significantly impaired in their ability to grow in nude mice. After 21 days, the volumes of the tumors from HiMut.1 and HiMut.2 were only 12–16% of the size of the tumors from the parental cells. Tumors derived from the C6 parental cells and vector control cells were essentially identical indicating that G418 selection of the vector control cells did not affect their ability to grow in nude mice. Tumors derived from HiMut.1 gave very dark immunological staining in at least 10% of the cells. HiMut.2-derived tumors were stained in 45–85% of the cells. The presence of the truncated PDGF-β receptor was also confirmed by Western blotting of lysed tumor sections. Thus, the truncated PDGF-β receptor was expressed in vivo for up to 21 days and it had to be present in at least 10% of the cells to be inhibitory. These studies demonstrate the usefulness of dominant negative mutants of PDGF-R to inhibit growth of tumors characterized by inappropriate PDGF-R activity in vivo.

Example 10

Chemical Synthesis

Some of the compounds of this invention may be prepared by employing procedures known in the literature starting from known compounds or readily made intermediates. Quinoxalines compounds were prepared by either 1) reacting 1,2 aromatic diamine with α-ketoaldehyde or α-diketone, or 2) an exchange reaction of α-bis thiosemicarbazones and a 1,2-diamine in the presence of an acid catalyst. In the following preparations the aromatic diamine was obtained commercially or prepared as described in the example. In examples where the reaction solvent is not specified, the reaction was carried out in ethanol-acetic acid. Some quinoxalines synthesized using this solvent were isolated as acid addition complexes with one molecule acetic acid, based on elemental analysis. Reactions in ethanol alone, followed by solvent evaporation and recrystallization, gave a cleaner product and higher yield.

Group 1 Compounds

A10

A10 can be prepared as in European Patent Application 0 013 376 A2. Alternatively A10 can be prepared as follows:

Step 1: Preparation of acetoacetic acid-(4-trifluoromethyl)aniline

A mixture of 4-trifluoromethylaniline (16.1 g, 0.1 mol), 2,2,6-trimethyl-4H-1,3-dioxin-4-one (purity 95%; 14.97 g, 0.1 mol), and xylene (20 ml) was heated to reflux for 30 minutes in a bath preheated to 150° C. The resulting dark solution was cooled to room temperature to crystalize the product. The crystals were filtered and collected. More material was obtained from mother liquors (the solution remaining after the initial crystallization and filtration). The yield of crude anilide was 17.75 g (72%), the anilide had a melting point of 153°–154° C.

Step 2: Preparation of 2-Ethoxymethyleneacetoacetyl-(4-trifluoromethyl)aniline.

Acetoacetyl-(4-trifluoromethyl)aniline (14.11 g., 57.6 mmol), triethoxymethane (9.43 g, 63.4 mmol), and acetic anhydride (16.30 ml, 173 mmol) were mixed together and heated to reflux for 90 minutes. The resulting dark solution was evaporated to dryness. The residue was resuspended in benzene/isooctane and the product was crystallized. More material was obtained from mother liquors. Yield of pure product was 11.93 g (72%), m.p. 120°–122° C.

Step 3: Preparation of A10

2-Ethoxymethyleneacetoacetyl-(4-trifluoromethyl)aniline (3.01 g, 10.4 mmol) in ethanol (6 ml) was slowly added to an ice cooled solution of hydroxylamine hydrochloride (0.77 g, 11.0 mmol) in 2M NaOH (5.5 ml). The mixture was heated to reflux for 1 hour, cooled to room temperature and evaporated to dryness. The residue was resuspended, and distributed between ethyl acetate and water. The organic layer was separated, extracted with water, dried by sodium sulfate and the solvent was evaporated. The residue was resuspended in toluene and crystallized to yield a solid residue (2.45 g, 87%) of A10 having a melting point of 166°–167° C.

A10

Preparation of 5-Methyl-isoxasole-4-carboxylic acid-(3-trifluoromethyl)-anilide was carried out in three steps:

a) Preparation of Acetoacetic acid —(3-trifluoromethyl)-anilide.

In a 25 ml round bottom flask equipped with Claisen distillation head and magnetic stirrer 4 g (18.6 mM) of α,α,α-Trifluoro-p-toluidine, 3.71 g (24.8 mM, 1 equiv.) 95% 2,2,6-trimethyl-4H-1,3-dioxin-4-one, 112 µl diethanoiamine and 12.4 ml xylene was combined. The temperature of the mixture was raised to 110° C., and the mixture was stirred at this temperature for 6 hours while acetone was distilled off from the system. The progression of the reaction was monitored by TLC (plate Merck Kieselgel 60 $F_{254}$ eluent: Petroleum ether (90°–110° C. fraction):acetone 2:1) visualization with 5% PMA in EtOH).

After 6 hours the xylene was distilled off at 20 Hgmm and the residue was purified with medium pressure (2 atm) liquid chromatography using Silica gel 60 as fixed phase and petroleum ether (90°–110° C. fraction):acetone 2:1 as eluent.

The product fractions at $R_f$=0.3 were collected—using the TLC system used for the monitoring of the reaction—and after stripping the solvent, 3.82 g of Acetoacetic acid—(3-trifluoromethyl)-anilide was isolated. Melting point: 91°–92° C.

$^1$H-NMR (ppm, acetone-d6) ArH 7.36–7.87 4H (m) NH 9.41 1H (s) $CH_2$ 3.62 2H (s) $CH_3$ 2.64 3H (s)

b) Preparation of 2-propenamide, 2-acetyl-3-ethoxy-N-[(trifluoromethyl)phenyl].

In a dried (120° C., 30 min) 50 ml round bottom flask equipped with magnetic stirrer, thermometer, rubber septum and Argon balloon on a T stopcock, 1.0 g (4.1 mM) Acetoacetic acid-(3-trifluoromethyl)-anilide, 0.85 g (5.7 mM) orthoformic acid triethylesther 1.37 g acetic anhydride and 450 mg dry zinc chloride was combined. The mixture was stirred in argon atmosphere at 60° C. for 30 minutes. The progress of the reaction was monitored by TLC (plate Merck Kieselgel 60 $F_{254}$, eluent: Petroleum ether (90°–110° C. fraction):acetone 5:1. If the reaction was not complete after 30 minutes, a further 0.85 g (5.7 mM) of orthoformic acid triethylesther was added.

The reaction mixture gradually turned brown. After the completion of the reaction, the reaction mixture was stripped in vacuo, the residue was dissolved in ethyl acetate, which was washed with water, the organic phase was dried with magnesium sulfate then filtered and the ethyl acetate was distilled off in vacuo. The 1.16 g crude product was purified with medium pressure (2 atm) liquid chromatography using Silica gel 60 as fixed phase and petroleum ether (90°–110° C. fraction):acetone 5:1 as eluent.

The product fractions at $R_F$=0.231 were collected—using the TLC system used for the monitoring of the reaction—and after stripping the solvent, 0.46 g of 2-propenamide, 2-acetyl-3-ethoxy-N-[(trifluoromethyl)phenyl] was isolated. Melting point: 100.5° C.

$^1$H-NMR (ppm, acetone-d6) ARH 7.29–8.00 4H (m) NH 11.25 1H (s) CH=8.46 1H (s) EtCH$_2$4.37 2H (s) EtCH$_3$1.45 3H (s) AcMe 2.48 3H (s)

c) Preparation of 5-Methyl-isoxasole-4-carboxylic acid-(3-trifluoromethyl)-anilide.

In a 25 ml round bottom flask equipped with magnetic stirrer and thermometer 0.11 g (1.58 mM) of hydroxylamine hydrochloride was dissolved in 0.5 ml of water and to this solution 64 mg (1.6 mM) sodium hydroxide was added in 0.5 ml of water. To this solution 2.2 ml of methanol was added and at room temperature 0.44 g (1.5 mM) 2-propenamide, 2-acetyl-3-ethoxy-N-[(trifluoromethyl)phenyl] was added. The progress of the reaction was monitored by TLC (plate Merck Kieselgel 60 F$_{254}$ eluent: Petroleum ether (90°–110° C. fraction):acetone 4:1, visualization with 5% PMA in EtOH. After completion of the reaction, the reaction mixture was concentrated in vacuo and the residue was dissolved in ethyl acetate. The organic phase was washed with water, dried with magnesium sulfate, filtered and concentrated. The obtained 0.51 g crude product was purified with medium pressure (2 atm) liquid chromatography using Silica gel 60 as fixed phase and petroleum ether (90°–110° C. fraction):acetone 4:1 as eluent.

The product fractions at $R_F$=0.162 were collected—using the TLC system used for the monitoring of the reaction—and after the stripping of the solvent, 0.22 g of 5-Methyl-isoxasole-4-carboxylic acid-(3-trifluoromethyl)-anilide was isolated. Melting point: 115°–120° C.

$^1$H-NMR (ppm, acetone-d6) ArH+NH 7.42–7.88 4H (m) CH=8.50 1H (s) CH 8.50 1H (s)

A12

A12 can be prepared as described by Patterson et al., *J. Med. Chem.* 35: 507–510 (1992).

Group 2 Compounds

B10

B10 was synthesized in two steps.

a) Synthesis of cyanoacetyl-(4-nitro)anilide.

1.38 g (10mmol) 4-nitroaniline was dissolved in 30 ml of absolute pyridine, then cooled to –30° C., 0.43 ml (5 mmol) phosphorus trichloride was added dropwise with continuous stirring to avoid increasing the temperature above –20° C. After 0.5 hour 0.85 g cyanoacetic acid was added, and the solution was stirred for 0.5 hour at –20° C. then 12 hours at room temperature.

The solvent was evaporated in vacuum. The residue was covered with 1N HCl and extracted with ethylacetate. The ethylacetate solution was dried over Na$_2$S$_4$, filtered and evaporated. The residue was triturated with ether filtered and dried in vacuo. 1.70 g (83%) product yield was obtained. The product had the following characteristics:

Melting point: 81°–83° C.

$R_F$: 0.95 (hexane-EtOAc; 1:1)

b. Acetylation of cyanoacetyl-(4-nitro)anilide.

0.82 g (4 mmol) cyanoacetyl 4-nitroanilide was dissolved in 2 ml absolute pyridine, followed by the addition of 20 mg 4-aminopyridine catalyst and 0.50 ml tetramethylguanidine. The reaction mixture was stirred while the nitroanilide dissolved. 5 ml of acetic anhydride was then dropped in at 0° C.

After 2 days the pyridine was evaporated, ethylacetate was added and the organic layer was extracted with 5% NaHC$_3$ solution, in 1N HCl, and water. The organic layer was dried over Na$_2$S$_4$ and evaporated. The residue was crystallized from ether and 210 mg (21% yield) of product was obtained. The product had the following characteristics:

$R_f$=0.35 (EtoAc)

Melting point: 260° C.

B11

2-Butenamide, 2-cyano-3-hydroxy-N-[(4-trifluoromethyl)phenyl]($C_{12}H_{19}F_3NO_3$) was prepared in two steps as follows:

a) Preparation of Cyanoacet-(4-trifluoromethyl)-anilide.

A mixture of 3 g (18.6mM) α,α,α-Trifluoro-p-toluidine and 3.37 g (29.8 mM, 1.6 equivalent) cyanoacetic acid ethyl ester in a 50 ml flask, equipped with magnetic stirrer, thermometer and nitrogen vent, was stirred on a 180° C. oil bath for 5 hours. The progress of the reaction was monitored by TLC (plate Merck Kieselgel 60 F$_{254}$, eluent: Petroleum ether (90°–110° C. fraction):acetone 1:1. The reaction mixture was purified with medium pressure (2 atm) liquid chromatography using Silica gel 60 as fixed phase and petroleum ether (90°–110° C. fraction):acetone 1:1 as eluent.

The product fractions were collected—using the TLC system used for the monitoring of the reaction—and after stripping the solvent, 2.11 g of Cyanoacet-(4-trifluoromethyl)-anilide was isolated. Melting point: 192°–194° C.

1 H-NMR (ppm, Acetone-d6) ArH 7.68–7.85 4H (dd) NH 9.84 H (s) CH$_2$3.90 2H (s)

b) Preparation of 2-Butenamide, 2-cyano-3-hydroxy-N-[(4-trifluoromethyl)phenyl].

In a 50 ml round bottom flask equipped with magnetic stirrer, thermometer, a rubber septum and a T stopcock (with vacuum and Argon blanket balloon joints), 1.78 g (0.89 g, 37.1 mM) 50% NaH oily dispersion was suspended in 4 ml dry (from P$_2$O$_5$) acetonitrile. The suspension was cooled to 10° C. and while stirring at this temperature 2.72 g (11.9 mM) Cyanoacet-(4-trifluoromethyl)-anilide was added dissolved in 25 ml dry (from LiAlH$_4$) tetrahydrofuran in 10 minutes. The reaction mixture turned yellow, and was cooled down after the addition to –10° C., and then 1.05 g (13.11 mM, 1.1 equiv.) Acetylchloride was added in 20 minutes. During the addition, the temperature of the reaction mixture can not be higher than –5° C. The progress of the reaction was monitored by TLC (plate Merck Kieselgel 60 F$_{254}$, eluent: Petroleum ether (90°–110° C. fraction):acetone 1:1.

When the reaction was complete, the reaction mixture was stirred at 0° C. for 30 minutes, at 35° C. for 30 minutes and at 65° C. for another 30 minutes, then the reaction mixture was stripped in vacuo. The residue was dissolved in 30 ml distilled water, charcoaled at 80° C. and filtered. The resulting pale yellow filtrate was acidified with a 10% hydrochloric acid solution, the precipitated crystals were filtered, washed with water and dried. The crude crystals (2.51 g) were purified with medium pressure (2 atm) liquid chromatography using Silica gel 60 as fixed phase and petroleum ether (90°–110° C. fraction):acetone 1:1 as eluent.

The product fractions at Rf=0.138 were collected—using the TLC system used for the monitoring of the reaction—and after stripping the solvent, 1.99 g of 2-Butenamide, 2-cyano-3-hydroxy-N-[(4-trifluoromethyl)phenyl] was isolated.

TLC petroleum ether (90°–110° C.)/acetone 1/1=0.138.

1 H-NMR (ppm, DMSO-d6) ArH 7.65–7.78 4H (dd) NH 10.85 1H (s) CH$_3$ 2.26 3H (s) OH 6.39 1H (s)

B12

Preparation of 2-Propenamide, 2-cyano-3-hydroxy-3-(4-fluorophenyl)-N-[(4-trifluoromethyl)phenyl] ($C_{17}H_{10}F_4N_2O_2$ MW:350.3) was carried out as follows:

a) Preparation of Cyanoacet-(4-trifluoromethyl)anilide:

A mixture of 3 g (18.6 mM) α,α,α-Trifluoro-p-toluidine and 3.37 g (29.8 mM, 1.6 equivalent) cyanoacetic acid ethyl ester in a 50 ml flask, equipped with a magnetic stirrer, thermometer and nitrogen vent, was stirred on a 180° C. oil bath for 5 hours. The progress of the reaction was monitored by TLC (plate Merck Kieselgel 60 F$_{254}$, eluent: Petroleum ether (90°–110° C. fraction):acetone 1:1. The reaction mixture was purified with medium pressure (2 atm) liquid chromatography using Silica gel 60 as fixed phase and petroleum ether (90°–110° C. fraction):acetone 1:1 as eluent.

The product fractions were collected and after the stripping of the solvent, 2.11 g of cyanoacet-(4-trifluoromethyl)-anilide was isolated. The product had the following characteristics:

Melting point: 192°–194° C.

$^1$H-NMR (ppm, acetone-d6) ArH 7.68–7.85, 4H (dd) NH 9.84 1H (s) CH$_2$ 3.90 (s)

b) Preparation of 2-Proponamide, 2-cyano-3-hydroxy-3-(4-fluorophenyl)-N-[(4-trifluoromethyl)phenyl]:

In a 50 ml round bottomed flask equipped with magnetic stirrer, thermometer, a rubber septum and a T stopcock (with vacuum and Argon blanket balloon joints) 0.55 g (0.275 g, 11.4 mM) 50% NaH oily dispersion was suspended in 1 ml dry (from P$_2$O$_5$) acetonitrile. The suspension was cooled to 10° C. and under stirring at this temperature 1 g (4.4 mM) cyanoacet-(4-trifluoromethyl)-anilide, dissolved in 10 ml dry (from LiAlH$_4$) tetrahydrofuran, was added in 10 minutes. The reaction mixture was then cooled down to –10° C. and at this temperature 0.77 g (4.8 mM, 1.1 equiv.) 4-fluorobenzylchloride was added in 20 minutes. During the addition the temperature of the reaction mixture was not allowed to go higher than –5° C. The progress of the reaction was monitored by TLC (plate Merck Kieselgel 60 F$_{254}$, eluent: Petroleum ether (90°–110° C. fraction):acetone 1:1.

The reaction mixture was then stirred at 0° C. for 30 minutes, at 35° C. for 30 minutes and at 65° C. for another 30 minutes, then the reaction mixture was stripped in vacuo. The residue was dissolved in 30 ml distilled water, charcoaled at 80° C. and filtered. The resulting pale yellow filtrate was acidified with 10% hydrochloric acid solution, the precipitated crystals were filtered, washed with water and dried. Crude crystals (2.47 g) were purified with medium pressure (2 atm) liquid chromatography using Silica gel 60 as fixed phase and petroleum ether (90°–110° C. fraction):acetone 1:1 as eluent.

The product fractions at Rf=0.216 were collected and after the stripping of the solvent, 1.05 g of 2-Propenamide, 2-cyano-3-hydroxy-3-(4-fluorophenyl)-N-[(4-trifluoromethyl)phenyl] was isolated. The product had the following characteristics:

Melting point: 195° C. (dec). $^1$H-NMR (ppm, acetone-d6) ArH 7.36–8.13 8H (m) NH 9.5 1H (s) OH 16.5 1H (s)

B13

Preparation of 2-Propenamide, 2-cyano-3-hydroxy-3-cyclohexyl-N-[(4-trifluoromethyl)phenyl]($C_{17}H_{17}F_3N_2O_2$ MW: 338.3) was carried out as described for B12 substituting 0.71 g (4.8 mM, 1.1 equiv.) cyclohexylacetyl-chloride for 4-fluorobenzoylchloride. The resulting product had the following characteristics:

TLC: R$_f$=0.265 (petroleum ether (90°–110° C.):acetone, 1:1)

Melting point: 212° C. (dec.)

B14

Preparation of 2-cyano-3-hydroxy-3-(2,2,3,3-tetramethylcyclopropyl)-propanol-4-(trifluoromethyl) anilide was carried out as described for B12 above using 2,2,3,4-tetramethylcylopropylcarboxyl chloride for 4-fluorobenzoylchloride.

B15

Preparation of 2-Propenamide, 2-cyano-3-hydroxy-3-(pentafluorophenyl)-N-[(4-trifluoromethyl)phenyl] was carried out as described for B12 substituting 1.5 g (6.51 mM, 1.1 equiv.) pentafluorobenzoylchloride for 4-fluorobenzoylchloride. The resulting product had the following characteristics:

TLC: R$_f$=0.360 (petroleum ether (90°–110° C.):acetone, 1:1) Melting point: 157°–158° C.

B16

Preparation of 2-Propenamide, 2-cyano-3-hydroxy-3-((3-phenoxy)phenyl)-N-[(4-trifluoromethyl)phenyl] ($C_{23}H_{15}F_3N_2O_3$ MW: 424.4) was carried out as described for B12 substituting 1.65 g (4.8 mM, 1.1 equiv) 3-phenoxybenzoyl chloride for 4-fluorobenzoylchloride. The resulting product had the following characteristics:

TLC: P$_f$=0.300 (petroleum ether (90°–110° C.):acetone, 1:1) Melting point: 197°–198° C.

B17

Preparation of 2-Butenamide, 2-cyano-3-hydroxy-4-phenyl-N-[(4-trifluoromethyl)phenyl] was carried out as described for B12 substituting 0.68 g (4.8 mM, 1.1 equiv.) phenyl-acetyl chloride for 4-fluorobenzoylchloride. The resulting product had the following characteristics: TLC: R$_f$,0.165 (petroleum ether (90°–110° C.):acetone, 1:1) Melting point: 156°–158° C.

B18

Preparation of 2-Hexeneamide, 2-cyano-3-hydroxy-5-methyl-N-[(4-trifluoromethyl)phenyl] ($C_{15}H_{15}F_3N_2O_2$ MW: 312.3) was carried out as described for B12 substituting 0.58 g (4.8 mM, 1.1 equiv.) isovalerylchloride for 4-fluorobenzoylchloride. The resulting product had the following characteristics:

TLC: R$_f$0.323 (petroleum ether (90°–110° C.):acetone, 1:1) Melting point: 161°–163° C.

B19

Preparation of 2-Butenamide, 2-cyano-3-hydroxy-4,4-diphenyl-N-[(4-trifluoromethyl)phenyl]($C_{24}H_{17}P_3N_2O_2$MW: 422.4) was carried out as described for B12 substituting 1.12 g (4.8 mM, 1.1 equiv.) diphenylacetyl-chloride for 4-fluorobenzoylchloride. The resulting product had the following characteristics:

TLC: R$_f$=0.354 (petroleum ether (90°–110° C.):acetone, 1:1) Melting point: 195°–202° C.

Group 3 Compounds

C10

340 mg (1.5 mM) 1-phenyl-3-amino-4-cyano-5-cyanomethyl-2-pyrazole, 210 mg (1.5mM) 3,4-dihydroxybenzaldehyde and 4 drops of piperidine in 30 ml ethanol were refluxed for 6 hours. Cooling and filtering gave 145 mg yellow solid. Evaporation of the solvent and trituration with $CH_2Cl2$-acetone gave another 145 mg yellow solid (56% yield). The product had a melting point of 147° C. NMR acetone $d_6$ δ–7.87 (1H,S, Vinyl), 7.68 (1H,d, J=2.2 $H_z$, $H_2$) 7.66–7.45 (5H,m, Ph), 7.28 (1H,dd, J=8.3.2.2 $H_2$, $H_6$). 6.92 (1H,d,J=8.3 $H_z$, $H_5$).

C11

C11 was synthesized using a two step procedure.

a. Synthesis of 3-amino-4-cyano-5-cyanomethyl-2 pyrozole:

2.2 g malononitrile dimer and 0.9 ml $N_2H_4$ in 20 ml of water were heated for 15 minutes at 100° C. Cooling and filtering gave 1.5 g (61% yield) of a white solid having a melting point of 187° C. (NMR acetone $d_6$ δ3.88 (s).) (Cf. Carboni et al., *J. Am. Chem. Soc.* 80: 2838 (1958), reporting m.p. 197° C.)

b. Condensation with dihydroxybenzaldehyde:

To 0.28 g (2 mM) 3,4-dihydroxybenzaldehyde and 1.33 g (2.2 mM) of 3-amino-4-cyano-5-cyanomethyl-2 pyrozole in 20 ml ethanol were added three drops piperidine and the reaction was refluxed 3 hours. Cooling, filtering and washing with ethanol gave 1.3 g (56% yield) of a yellow solid having a melting point of 300° C.

Group 4 Compounds

D11

435 mg (3 mM) 3-formyl indole, 300 mg (4.5 mM) 2-thiocarboxamido acetonitrile and 20 mg β-alanine in 30 ml ethanol were refluxed for six hours. Cooling and filtering gave 0.47 g (81% yield of a yellow solid having a melting point of 238° C.

D12

This was synthesized as for D11 except 1,1,4-tricyano-2-amino-1-propene was used instead of the acetonitrile derivative. The final product had a melting point of 293° C.

D13

This was synthesized as for D11 except 2-carboxamidoacetonitrile was used instead of the acetonitrile derivative. The final product had a melting point of 242° C.

D14

0.29 g (2 mM) 3-formyl indole, 0.29 g (2 mM), 3-amino-4-cyano-5-cyanomethyl-2-pyrazole and 20 mg β-alanine in 30 ml of ethanol were refluxed 4 hours. Cooling and filtering gave 0.34 g (62% yield) of yellow solid having a melting point of 281° C.

NMR acetone $d_6$ 8.52 (1H, S, vinyl), 8.42 (1H,S,$H_2$), 7.79 (1H,m), 7.57 (1H,m), 7.27 (2H,m), 6.17 (1H, br.S, NH). MS-274 (M+, 100%), 219(14), 91(35), m/e.

D15

0.3 g (1.3 mM) 3-amino-4-cyano-5-cyanomethyl-2-pyrazole, 0.2 g (1.36 mM) of 1-(3-dimethylaminopropyl)-3-formyl indole and 20 mg β-alanine in 20 ml ethanol were refluxed 4 hours. Evaporation, trituration with benzene and filtering gave 0.4 g of yellow solid (94% yield) containing 10% 3-amino-4-cyano-5-cyanomethyl-2-pyrazole. 0.4 g was chromatographed on silica gel (70–220 mesh) eluting with 85:15 methylene chloride:methanol to give 0.12 g of a bright yellow solid having a melting point of 250° C.

NMR acetone $d_6$ δ8.45 (1$H_1S_1$Vinyl), 8.37 (1$H_1S_1H_2$), 7.78 (1$H_1$m), 7.60(1$H_1$m). 7.28(2$H_1$m), 4.47(2$H_1t_1$J= 6.8$H_z$), 2.29(2$H_1t_1$J=6.8 $H_z$), 2.24(6H, S,N-($CH_3)_2$). MS-360(M+1, 8%), 359(M+,31), 289(100), 261(15), 144(6), m/e.

D16

0.4 g (1.7 mM) 3-amino-4-cyano-5-cyanomethyl-2-pyrazole, 0.3 g (1.73 mM) 1-oxo-1-(3,4-dihydroxyphenyl)-2-cyanothane and 20 mg β-alanine in 20 ml ethanol were refluxed 5 hours. Cooling and filtering gave 0.1 g of a brown solid. Preparative chromatography gave 20 mg (3% yield) of an orange solid having a melting point of 115° C.

NMR acetone $d_6$δ8.72(1H, S, Vinyl), 8.52(1$H_1$ $S_1$ $H_2$), 7.90(1$H_1$m), 7.73(1H,m), 7.40(4H,m), 7.0(1H,d,J=8.2 $H_2$, $H_5$). 4.57(2H,t,J=7.2 $H_z$), 2.46(2H,t,J=7.2 $H_z$), 2.34(6H,S,N ($CH_3)_2$), 2.17 (2H, quintet, J=7.2 $H_z$).

D17

0.4 g (2 mM) 3-formyl indole, 0.36 g 1-oxo-1-(3,4-dihydroxyphenyl)-2-cyanothane and 3 drops of piperidine, in 25 ml ethanol, were refluxed 6 hours. Workup and trituration with benzene gave 0.36 g of a yellow solid having a melting point of 225° C.

NMR acetone $d_6$ 8.77(1H,S), 7.90(1H,m), 7.70(1H,m), 7.40(4H-m), 7.0(2H,t,J=6.7$H_z$), 4.92(2H,t,J=6.8$H_z$), 3.26 (2H,t,J=6.8-$H_z$).

Group 5

Group 5 compounds were prepared in three steps.

a) Preparation of N-aryl-oxamic acid esters (=Ethyloxalyl anilides):

0.025 mol (3.4 ml) diethyl-oxalate and 0.1 mol of the appropriate aniline were mixed together and refluxed at 190° C. for 15 minutes. The resulting solution was cooled and left overnight to crystallize the product. The crystals were filtered, washed with ethanol and extracted with hot ethanol. The insoluble material was filtered off and the solution put in the refrigerator. The resulting crystals were filtered and dried.

TABLE XV

| No. | Subs. | MP °C. | Formula: | MW | Yield [%] |
|---|---|---|---|---|---|
| 1a | 4-N(CH$_3$)$_2$ | 116–118 | C$_{12}$H$_{16}$N$_2$O$_3$ | 236.27 | 75 |
| 1b | 3-OH | 184–185 | C$_{10}$H$_{11}$NO$_4$ | 209.20 | 86 |
| 1c | 2-OCH$_3$ | 81–82 | C$_{11}$H$_{13}$NO$_4$ | 223.23 | 60 |
| 1d | 2-OC$_2$H$_5$ | 74–76 | C$_{12}$H$_{15}$NO$_4$ | 237.26 | 64 |
| 1e | 3-NO$_2$ | 93–96 | C$_{10}$H$_{10}$N$_2$O$_5$ | 238.20 | 53 | b) Preparation of N-aryl-oxamic acid hydrazides (N-aryl-oxamoyl hydrazides)

0.05 mol of the appropriate N-aryl-oxamic acid ester (1a ... 1e) was dissolved in 200 ml of ethanol and slowly added to a well-stirred solution of 7.5 ml (~0.15 mol) hydrazine hydrate in 50 ml ethanol. The mixture was left at room temperature for 48 hours. The resulting heterogeneous solution was refluxed for 15 minutes and filtered the hot solution. After cooling to room temperature the precipitated substance was filtered washed with ethanol and dried.

TABLE XVI

| No. | Subs. | MP °C. | Formula: | MW | Yield [%] |
|---|---|---|---|---|---|
| 2a | 4-N(CH$_3$)$_2$ | 228–232 | C$_{10}$H$_{14}$N$_4$O$_2$ | 222.25 | 83 |
| 2b | 3-OH | 200–202 | C$_8$H$_9$N$_3$O$_3$ | 195.18 | 72 |
| 2c | 2-OCH$_3$ | 165–167 | C$_9$H$_{11}$N$_3$O$_3$ | 209.21 | 67 |
| 2d | 2-OC$_2$H$_5$ | 152–154 | C$_{10}$H$_{13}$N$_3$O$_3$ | 223.23 | 58 |
| 2e | 3-NO$_2$ | 231–234 | C$_8$H$_8$N$_4$O$_4$ | 224.18 | 49 | c) Preparation of N-aryl-oxamoyl hydrazones:

E10

0.001 mol (0.222 g) of N-(4-dimethylamino)-phenyloxamoyl hydrazide (2a) was dissolved in 5 ml acetic acid and heated at 100° C. with 0.001 mol (0.138 g) of 3,4-dihydroxy benzaldehyde for 20–25 minutes in the presence of a catalytic amount of sodium acetate. The mixture then cooled and left overnight at room temperature. The separated crystals were filtered off and washed with acetic acid and water.

Yield of pure product was 0.23 g (68%) m.p. 253° C. (C$_{17}$H$_{18}$N$_4$O$_4$, MW:342.36)

Elemental Analysis [%]: Found C, 59.51: H, 5.28; N, 16.25 Calculated C, 59.64; H, 5.30; N, 16.37.

E11

0.001 mol (0.195 g) of N-3-hydroxy-phenyloxamoyl hydrazide (2b) was dissolved in 5 ml acetic acid and heated at 100° C. with 0.001 mol (0.138 g) of 3,4-dihydroxy benzaldehyde for 20–25 minutes in the presence of a catalytic amount of sodium acetate. The mixture was then cooled and left overnight at room temperature. The separated crystals were filtered off and washed with acetic acid and water.

Yield of pure product was 0.142 g (45%) m.p. >260° C. (C$_{15}$H$_{13}$N$_3$O$_5$, MW:315.29).

Elemental Analysis [%]: Found C, 57.06; H, 4.10; N, 13.20. Calculated C, 57.14; H, 4.16, N, 13.33

E12

0.001 mol (0.195 g) of N-3-hydroxyphenyl-oxamoyl hydrazide (2b) was dissolved in 5 ml acetic acid and heated at 100° C. with 0.001 mol (0.122 g) of 2-hydroxy-benzaldehyde for 20–25 minutes in the presence of a catalytic amount of sodium acetate. The mixture was then cooled and left overnight at room temperature. The separated crystals were filtered off and washed with acetic acid and water.

Yield of pure product was 0.224 g (75%) m.p. 264°–266° C. (C$_{15}$H$_{13}$N$_3$O$_4$, MW:299.29)

Elemental Analysis [%]: Found C, 60.11; H, 4.40; N, 13.76. Calculated C, 60.20; H, 4.38; N, 14.04

E13

0.001 mol (0.21 g) of N-2-methoxyphenyl-oxamoyl hydrazide (2c) was dissolved in 5 ml acetic acid and heated at 100° C. with 0.001 mol (0.138 g) of 3,4-dihydroxy-benzaldehyde for 20–25 minutes in the presence of a catalytic amount of sodium acetate. The mixture was then cooled and left overnight at room temperature. The separated crystals were filtered off and washed with acetic acid and water.

Yield of pure product was 0.21 g (64%) m.p. 232°–238° C. (C$_{16}$H$_{15}$N$_3$O$_3$, MW:329.31). Elemental Analysis [%]: Found C, 60.01; H, 4.51; N, 12.59. Calculated C, 58.36; H, 4.59; N, 12.72.

E14

0.001 mol (0.22 g) of N-2-ethoxyphenyl-oxamoyl hydrazide (2d) was dissolved in 5 ml acetic acid and heated at 100° C. with 0.001 mol (0.138 g) of 3,4-dihydroxy-benzaldehyde for 20–25 minutes in the presence of a catalytic amount of sodium acetate. The mixture was then cooled and left overnight at room temperature. The separated crystals were filtered off and washed with acetic acid and water.

Yield of pure product was 0.15 g (44%) m.p. 208°–214° C. (C$_{17}$H$_{17}$N$_3$O$_5$, MW:343.34). Elemental Analysis [%]: Found C, 59.78; H, 4.81; N, 12.10. Calculated C, 59.47; H, 4.99; N, 12.24

E15

0.001 mol (0.22 g) of N-3-nitrophenyl-oxamoyl hydrazide (2e) was dissolved in 5 ml acetic acid and heated at 100° C. with 0.001 mol (0.138 g) of 3,4-dihydroxy-benzaldehyde for 20–25 minutes in the presence of a catalytic amount of sodium acetate. The mixture was then cooled and left overnight at room temperature. The separated crystals were filtered off and washed with acetic acid and water.

Yield of pure product was 0.19 g (56%) m.p. >260° C. (C$_{15}$H$_{12}$N$_4$O$_6$, MW:344,286). Elemental Analysis [%]: Found C, 52.08; H, 3.47; N, 16.10. Calculated C, 52.32; H, 3.51; N, 16.27.

E16

0.001 mol (0.22 g) of N-3-nitrophenyl-oxamoyl hydrazide (2e) was dissolved in 5 ml acetic acid and heated at 100° C. with 0.001 mol (0.122 g) of 4-hydroxy-benzaldehyde for 20–25 minutes in the presence of a catalytic amount of sodium acetate. The mixture was then cooled and left overnight at room temperature. The separated crystals were filtered off and washed with acetic acid and water.

Yield of pure product was 0.19 g (61%) m.p. >260° C. (C$_{15}$H$_{12}$N$_4$O$_5$, MW:328.29). Elemental Analysis [%]: Found C, 54.80; H, 3.59; N, 16.86. Calculated C, 54.88; H, 3.68; N, 17.07.

Group 6 compounds

F10

F10 can be prepared using a two step approach.

a) Preparation of 2-methyl-3-hydroxyethyl quinazolin-4-one:

1.37 g (0.01 mol) anthranilic acid was refluxed with 8 ml acetic anhydride for 3 hours. The formed acetic acid was distilled off continuously at atmospheric pressure. After the acetic acid formation was finished the mixture was evaporated in vacuo to dryness. The resulting oil was mixed with 2 ml of ethanolamine and heated at 160° C. for 3 hours. After the reaction was completed the substance was cooled, mixed with alcohol and left at room temperature overnight. The precipitated crystals were collected by filtration. m.p. 159°–60° C.; 1.40 g (65%).

Step b 1.08 g (0.005 mol) 2-methyl-3 hydroxyethyl-quinazolin-4-one and 0.69 g 3,4-dihydroxy-benzaldehyde were fused at 160° C. and heated for additional 30 minutes. The resulting substance was dissolved in isopropanol, decolorized by charcoal and left at room temperature overnight. The precipitated crystals were filtered and dried. Yield of pure product was 0.79 g (49%) m.p. 221°–223° C. (C$_{18}$H$_{16}$N$_2$O$_4$, MW:324.34) Elemental Analysis [%]: Found C, 66.48 H, 4.86; N, 8.62. Calculated C, 66.66; H, 4.97; N, 8.64.

F11 and F12

1.01 g (5 mmol) of 3,4-dihydro-1,4-oxazine-[3,4-b] quinazolin-6-one were fused with 6mmol of the corresponding benzaldehyde derivative on an oil bath at a temperature of 100°–200° C. After removal of the water of reaction, the resulting mixture was dissolved in ethanol and clarified with charcoal. The solvent was evaporated and the product recrystallized.

For preparation of F11, 3,4-dihydroxybenzaldehyde was used to obtain the product (85% yield) having a melting point of 290°–292° C.

For preparation of F12 3-hydroxybenzaldehyde was used to obtain the product (63% yield) having a melting point of 208°–214° C.

Group 7 Compounds

G10

0.4 g (4 mM) phenylene diamine and 0.6 g (4 mM) phenyl glyoxal monohydrate in 20 ml of ethanol, and 10 ml acetic acid was refluxed 3 hours. Workup using 50 ml $H_2O$ and 80 ml $CH_2Cl_2$ followed by trituration with hexane gave 0.38 g (46% yield) of a white solid having a melting point of 65° C.

NMR $CDCl_3$ $\delta9.44$ (1H, S), 8.1 (4H,m), 7.8(2H,m),7.6 (3H,m). MS-206 (M+, 100%), 179 (M-HCN, 25), 152 (37), 103 (M -Ph-CN, 42), m/e.

G12

To 3 ml DMF and 16 ml $PCCl_3$ was added 2.7 g (10 mM) N-(3,4-dimethoxyphenyl)phenylacetamide. The reaction was heated at 90° C. for 4 hours, decanted on ice, filtered and washed with water to give 2.9 g (96% yield) of a white solid having a melting point of 234° C.

NMR $CDCl_3$): $\delta8.26$ (1H, s $h_4$), 8.0 (1H, s, $H_8$), 7.15 (5H, s Ph), 7.15 (1H, s, $h_5$), 4.13, 4.05 (6H, 2s, $OCH_3$). MS: 301, 299 (M+, 33%, 100%), 286, 284 (M-$CH_3$, 2%, 6%), 258, 256, (6%, 18%), 220 (9%), 215, 213 (4%, 13%), m/e.

G11

The compound was synthesized by the procedure used for G12, except that the reactant N-(3,4,5-trimethoxy phenyl) phenylacetamide was substituted. The final product had a melting point of 103° C.

G13

2.4 g (16 mM) phenyl glyoxal hydrate and 2.2 g (16 mM) 3,4-dimethyl-i, 2-phenylene diamine in 20 ml ethanol were refluxed for 1.5 hour. Cooling and filtering gave 3.25 g (88% yield) of a white solid having a melting point of 124° C.

NMR $CDCl_3$ $\delta9.23$(1H,S,H2), 8.19(1H,d,J=1.6$H_2$), 8.15 (1H,d,J=1.7$H_2$), 7.90(2H,d,J=9.0 $H_2$), 7.57(3H,m)2.52(6H, S,$CH_3$). MS-234 (M+, 100%), 219 (M-$CH_3$, 11), 207 (M-HCH, 12), 165 (M-2HCN-$CH_3$,2), 131(M-ph-CN,3), m/e.

G14

7 g of veratrole (51 mM) was added to 19 ml of ice-cooled 70% $HNO_3$. After 0.5 hour in the cold, 10 ml $H_2SO_4$ was slowly added in 0.5 hour. The resulting dark suspension was stirred for 3 hours at room temperature and ice and water were added to the suspension to precipitate the product. Filtering, washing with water and drying gave 10.2 g (96% yield) of a yellow solid having a melting point of 120° C. (NMR $CDCl_3$ $\delta7.35$(2H,S), 4.06(6H,S,$OCH_3$)). (Cf: *J. Org. Chem.* 12: 522 (1947), reported m.p. 130° C., and *J. Med. Chem.* 36: 331 (1993) reported m.p. 122° C. The compound is sold by Lancaster Co., (reported m.p. 101° C.).

Two grams of 1,2-dinitro-4,5-dimethoxybenzene was hydrogenated over 0.3g $PtO_2$ for 1 hour, then filtered and evaporated to give 1.5 g of a black solid (Cf. *J. Med. Chem.* 36: 331 (93), reported red brown solid, m.p. 151° C.). The black solid was mixed with 1.3 g phenyl glyoxal, 15 ml absolute ethanol and 15 ml of concentrated HCl and refluxed 5 hours. Workup, as for G10, gave a dark solid which was recrystallized from ethanol to give 0.72 g (31% yield) of a white solid having a melting point of 134° C.

NMR $CDCl_3$ $\delta9.13$(1H,S,$H_2$), 8.16(1H,d,J=1d.6$H_2$), 7.60–7.40 (5H,m), 4.09 (6H, S,$OCH_3$).

MS-266 (M+, 100%), 251 (M-$CH_3$, 12), 223 (M-$CH_3$-CO, 13), 196 (M-$CH_3$-CO-HCN, 5), m/e.

G15

Thiophene-2-glyoxal-bis-thiosemicarbazone (3.4 mM) and 0.6 g (4 mM) o-phenylenediamine in 15 ml acetic acid were refluxed 6 hours. The solvent was removed by distillation in vacuo, and the residue was dissolved in $CH_2Cl_2$ and washed with $H_2O$. The organic layer was evaporated in vacuo and the residue was triturated with benzene-hexane to give a white solid (23% yield) mp 104° C.

NMR ($CDCl_3$): $\delta9.25$(1H, s, $H_2$), 8.07, 7.72(4H, m, $H_{5-8}$), 7.85, 7.56, 7.21(3H, m, thiophene). MS: 212($M^+$, 100%), 185(M-HCN, 25%), 141(6%), 106(8%), m/e.

G16

2,3-diaminopyridine and phenyl glyoxal were reacted as for G13 to give a white solid (77% yield) having a melting point of 135° C.

NMR $CDCl_3$ $\delta9.47$(1H,S,$H_2$), 9.21 8.50, 7.71 (8 line ABC m, $H_7,H_5,H_6$), 8.35(2H,m,Ph), 7.60(3H,m).

MS-207 (M+, 100), 180 (H-HCN, 8), 179 (11), 104 (23), 77 (14),m/e. $CDCl_3$ $\delta7.67$(1H, dd), 6.89(dd), 6.62(dd), 4.25, 3.30 (br.S.).

G17

G17 was synthesized in two steps as follows:

a. Synthesis of 2-methoxy-4,5-dinitro phenol.

3.3 g 1,2-dimethoxy-4,5-dinitrobenzene in 20 ml of 48% HBr was refluxed for 16 hours. Water was added and the reaction was extracted with $CH_2Cl_2$ to give 1.1 g of an orange solid. Chromatography on silica gel, eluting with 2% $CH_3OH$ in $CH_2Cl_2$ gave 0.42 g (13% yield) of a yellow solid which turned red with KOH.

NMR ($CDCl_3$): $\delta7.44$(1H, s), 7.42(1H, s), 6.30(1H,s), 4.07(3H,s).

Extraction of the aqueous phase with ethyl acetate gave 2 g of a red oil. Chromatography on silica gel, eluting with 5% $CH_3OH$ in $CH_2Cl_2$ gave a yellow solid, 0.1 g (3.5% yield) having a melting point of 160° C. with a KOH violet color, corresponding to 1,2 dihydroxy-4,5-dinitrobenzene.

NMR (acetone-$d_6$) $\delta7.51$(2H,s).

b. Reduction and condensation with phenylglyoxal.

0.2 g 2-methoxy-4,5-dinitrophenol was hydrogenated on Pd/C in 20 ml ethanol for one hour. The Pd was filtered, 0.3 g phenyl glyoxal was added, and the reaction was refluxed for three hours. Evaporation and chromatography on silica gel, eluting with 1% $CH_3OH$ in $CH_2Cl_2$ gave a 0.1 g of an orange oil.

NMR ($CDCl_3$): $\delta8.10$, 7.6(7H,m), 3.54(3H,S).

G18

0.56 g (4 mM) 4,5-dimethyl 1,2-diaminobenzene and 0.6 g (4 mM) benzoyl formic acid in 15 ml ethanol were refluxed 5 hours. Cooling and filtering gave 0.8 g (80% yield) of a yellow solid having a melting point of 275° C. NMR ($CDCl_3$): $\delta8.38$(2H, m), 7.51(3H, m), 7.70(1H, s), 7.06(1H, s) 2.40(3H, s), 2.37(3H, s). Irradiation at 8.38 ppm gave a Singlet at 7.51 ppm.

G19

3,4-diaminotoluene and phenyl glyoxal were reacted as for G13 to give a light brown solid (31% yield) having a melting point of 114° C.

NMR $CDCl_3$ $\delta9.29$, 9.26(2S,2:1,$H_2$), 8.2, 8.17(2br. S), 8.07–7.90(3H,m), 7.60(3H,m),2.62(3H,S).

G20

0.15 g of G14 in 5 ml 48% HBr was refluxed 23 hours. Cooling and filtering gave 95 mg (53% yield) of a green-yellow solid corresponding to the HBr salt of the quinazoline derivative, mp 280° C. HBr was determined by elemental analysis.

NMR (DMSO-$d_6$): δ9.25(1H, s, $H_2$), 8.24(1H, d, J=1.9 Hz), 8.20(1H, d, J=1, 9 Hz), 7.50(3H, m), 7.35(2H, m).

The mother liquid was neutralized with $NaHCO_3$. Extraction with EtAc gave 20 mg (15% yield) of an orange solid, mp 305° C. corresponding to the free base.

NMR (acetone $d_6$): δ9.19(1H s, $H_2$), 8.29(1H, d, J=1.5 Hz), 8.25(1H, d, J=1.5 Hz), 7.6(3H, m), 7.40(2H, m).

MS: 238(M+, 54%), 211(M-HCN, 10%), 154(7%), 108 (1,2-benzoquinone, 100%), m/e.

G21

4-Benzoyl 1,2-phenylene diamine and phenyl glyoxal were reacted as for G13 to give a white solid (69% yield) having a melting point of 133° C.

NMR: $CDCl_3$ δ9.40(1H,S,$H_2$), 8.49(1H,S,$H_5$), 8.27(4H, br,S,$H_{7,8}H_{-2',6'}$), 7.90(2H,d,J=7.6 $H_2$), 7.60(6H,m).

G22

0.47 g (3 mM) 2,3-diaminoaphtalene and 0.47 g phenyl gloxal hydrate in 20 ml ethanol were refluxed for 1.5 hour. Cooling and filtering gave 0.5 g (65% yield) of a light brown solid having a melting point of 163° C. NMR: $CDCl_3$ δ9.38(1H, S,$H_2$), 8.71,8.67(2H,2d,$H_{5,10}$), 8.25,8.10-(4H, AA'BB'm.,$H_{6,9}$), 7.58(5H,m,Ph), MS-256 ($H^+$, 100%), 229 (H-CN, 12%), 126 (71), m/e.

Group 8

H10

0.01 mol (1.07 g) of benzylamine and 0.01 mol (1.38 g) of 3,4-dihydroxybenzaldehyde were mixed together in 15 ml of ethanol and refluxed on a waterbath for 15 minutes then 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanole.

Yield: 3.07 g (77%) M.p.:209°–211° C. Formula: $C_{24}H_{21}N_3O_3$ Elemental analysis [%]

Calculated: C: 72.17 H: 5.30 N: 10.52 Found: C: 72.12 H: 5.26 N: 10.46

H11

0.01 mol (1.07 g) of benzylamine and 0.01 mol (1.22 g) of salicylaldehyde were mixed together in 15 ml of ethanol and refluxed on a waterbath for 15 minutes then 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanole.

Yield: 2.99 g (78%) M.p.:189°–192° C. Formula: $C_{24}H_{21}N_3O_2$ Elemental analysis [%]

Calculated: C: 75.18 H: 5.52 N: 10.96 Found: C: 75.09 H: 5.49 N: 10.90

H12

0.01 mol (1.07 g) of benzylamine and 0.01 mol (1.22 g) of 3-hydroxybenzaldehyde were mixed together in 15 ml of ethanol and refluxed on a waterbath for 15 minutes then 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanole.

Yield: 2.72 g (71%) M.p.:184°–185° C. Formula: $C_{24}H21N_3O_2$ Elemental analysis [%]

Calculated: C: 75.18 H: 5.52 N: 10.96 Found: C: 75.02 H: 5.45 N: 11.08

H13

0.01 mol (1.07 g) of benzylamine and 0.01 mol (1.22 g) of 4-hydroxybenzaldehyde were mixed together in 15 ml of ethanol and refluxed on a waterbath for 15 minutes then 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanole.

Yield: 3.40 g (89%) M.p.:217°–219° C. Formula: $C_{24}H_{21}N_3O_2$ Elemental analysis [%]

Calculated: C: 75.18 H: 5.52 N: 10.96 Found: C: 75.26 H: 5.47 N: 10.88

H14

0.01 mol (1.07 g) of benzylamine and 0.01 mol (1.54 g) of 3,4,5-trihydroxybenzaldehyde were mixed together in 15 ml of ethanol and refluxed on a waterbath for 15 minutes then 0.01 mol (3.44 g) of 2-(1'-tosyloxyethyl)-quinazolin-4-one and one drop of pyridine were added and the mixture was refluxed for six hours. The resulting solution was evaporated and extracted with a 5% water solution of sodium bicarbonate. The remaining crystals were filtered off, washed with water and recrystallized from isopropanole.

Yield: 3.36 g (81%) M.p.:223°–225° C. Formula: $C_{24}H_{21}N_3O_2$ Elemental analysis [%]

Calculated: C: 69.39 H: 5.10 N: 10.11 Found: C: 69.51 H: 5.07 N: 10.08

Group 9

I10

0.3 g (2 mM) 5-formyl indole and 0.4 g (2 mM), of 2-cyano-H-(1-(+) phenylethyl)acetamide in 5 ml ethanol and 2 drops piperidine were refluxed 3 hours. Water and HCl were added and the reaction extracted with ethyl acetate to give viscous oil. Chromatography on silica gel gave 0.42 g (66% yield) of pale-yellow solid having a melting point of 76° C.

MS-315 (M+, 24%), 196 (M-NCH($CH_3$)$C_6H_5$, 22), 195 (25), 188 (21), 173 (24), 168 (13), 149 (57), 145 (100), 134 (92), (53), m/e.

Other embodiments are within the following claims.

We claim:

1. A method of treating a patient suffering from a carcinoma cancer characterized by inappropriate PDGF-R activity, comprising the step of administering to said patient a therapeutically effective amount of a composition comprising a compound selected from the group consisting of:

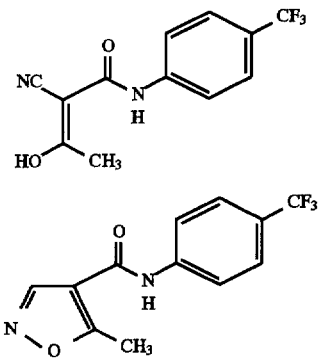

and pharmaceutically acceptable salts thereof.

2. The method of claim 1 wherein said compound is either:

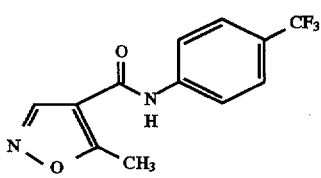

or pharmaceutically acceptable salts thereof.

3. The method of claim 1, wherein said compound is, either

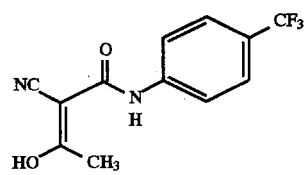

or pharmaceutically acceptable salts thereof.

4. A method of treating a patient having ovarian cancer characterized by inappropriate PDGF-R activity comprising the step of administering to said patient a therapeutically effective amount of a compound selected from the group consisting of;

5-methylisoxazole-4 carboxylic acid-(4-trifluromethyl)-anilide, N-(4-trifluoromethylphenyl)-2-cyano-3-hydroxycrotoamide, and pharmaceutically acceptable salts thereof.

5. The method of claim 2 or 3, further comprising the step of determining whether said cancer has an inappropriate PDGF-R activity.

6. A method of treating a patient having an intra-axial brain cancer characterized by inappropriate PDGF-R activity comprising the step of administering to said patient a therapeutically effective amount of a compound selected from the group consisting of:

5-methylisoxazole-4 carboxylic acid-(4-trifluromethyl)-anilide,

N-(4-trifluoromethylphenyl)-2-cyano-3-hydroxycrotoamide, pharmaceutically acceptable salts thereof.

7. A method of treating a patient having glioma characterized by inappropriate PDGF-R activity comprising the step of administering to said patient a therapeutically effective amount of a compound selected from the group consisting of:

5-methylisoxazole-4 carboxylic acid-(4-trifluromethyl)-anilide,

N-(4-trifluoromethylphenyl)-2-cyano-3-hydroxycrotoamide, and pharmaceutically acceptable salts thereof.

8. The method of claim 7, further comprising the step of determining whether said cancer has an inappropriate PDGF-R activity.

9. A method of treating a patient having colon cancer characterized by inappropriate PDGF-R activity comprising the step of administering to said patient a therapeutically effective amount of a compound selected from the group consisting of:

5-methylisoxazole-4 carboxylic acid-(4-trifluromethyl)-anilide,

N-(4-trifluoromethylphenyl)-2-cyano-3-hydroxycrotoamide, and pharmaceutically acceptable salts thereof.

10. A method of treating a patient having lung cancer characterized by inappropriate PDGF-R activity comprising the step of administering to said patient a therapeutically effective amount of a compound selected from the group consisting of:

5-methylisoxazole-4 carboxylic acid-(4-trifluromethyl)-anilide,

N-(4-trifluoromethylphenyl)-2-cyano-3-hydroxycrotoamide, and pharmaceutically acceptable salts thereof.

11. A method of treating a patient having prostate cancer characterized by inappropriate PDGF-R activity comprising the step of administering to said patient a therapeutically effective amount of a compound selected from the group consisting of:

5-methylisoxazole-4 carboxylic acid-(4-trifluromethyl)-anilide,

N-(4-trifluoromethylphenyl)-2-cyano-3-hydroxycrotoamide, and pharmaceutically acceptable salts thereof.

12. A method of treating a patient suffering from either a carcinoma characterized by inappropriate PDGF-R activity or an intra-axial brain cancer characterized by inappropriate PDGF-R activity, comprising the step of administering to said patient a therapeutically effective amount of a compound which forms, in vivo,

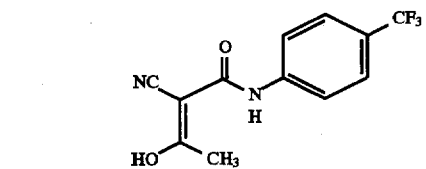

after administration to said patient.

13. The method of claim 12, wherein said cancer is intra-axial brain cancer.

14. The method of claim 12, wherein said cancer is ovarian cancer.

15. The method of claim 12, wherein said cancer is colon cancer.

16. The method of claim 12, wherein said cancer is prostate cancer.

17. The method of claim 12, wherein said cancer is lung cancer.

18. The method of claim 12, wherein said cancer is glioma.

19. The method of any of claims 1–10 and 11, wherein said compound is present in a pharmaceutical composition which comprises a physiological acceptable carrier comprising a first solution comprising about 3% w/v benzyl alcohol, about 8% w/v polysorbate 80, and about 65% w/v polyethylene glycol (MW=300 daltons) in absolute ethanol, diluted about 1:1 in a second solution comprising about 5% dextrose in water.

20. The method of any one of claims 4–10 and 11 wherein said compound is 5-methylisoxazole-4 carboxylic acid-(4-trifluromethyl)-anilide or a pharmaceutically acceptable salt thereof.

21. The method of any one of claims 4–10 and 11, wherein said compound is N-(4-trifluoromethylphenyl)-2-cyano-3-hydroxycrotoamide, or a pharmaceutically acceptable salt thereof.

22. A method of treating a patient having a cancer selected from the group consisting of: a carcinoma and an intra-axial brain cancer, wherein said cancer is characterized by inappropriate PDGF-R activity, comprising the step of administering to said patient a sufficient amount of a compound to reduce PDGF-R activity, said compound selected from the group consisting of 5-methylisoxazole-4 carboxylic acid-(4-trifluromethyl)-anilide, N-(4-trifluoromethylphenyl)-2-cyano-3-hydroxycrotoamide, and pharmaceutically acceptable salts thereof.

23. The method of claim 22, wherein said compound is either 5-methylisoxazole-4 carboxylic acid-(4-trifluromethyl)-anilide or pharmaceutically acceptable salts thereof.

* * * * *

UNITED STATES PATENT AND TRADEMARK OFFICE
CERTIFICATE OF CORRECTION

PATENT NO. : 5,700,823
DATED : December 23, 1997
INVENTOR(S) : Klaus Peter Hirth, et al.

It is certified that error appears in the above-indentified patent and that said Letters Patent is hereby corrected as shown below:

Column 5, Line 39: delete "1a-k" and insert --1a-i--.

Column 7, Line 46: delete "$R_{17}$" and insert --$R_{18}$--.

Column 8, Line 60: delete "=0or" and insert -- =0 or--.

Column 9, Line 40: delete "an" and insert --a--.

Column 13, Line 32: delete "possibly" and insert --possible--.

Column 13, Line 33: delete "Kemmerer" and insert --Kammerer--.

Column 13, Line 34: delete "Kemmerer" and insert --Kammerer--.

Column 21, Line 27: delete "3H-thymidine" and insert --$^3$H-thymidine--.

Column 24, Line 24: delete "IC50" and insert --$IC_{50}$--.

Column 25, Line 2: delete the "p" before the word Cell.

Column 25, Line 22: delete "mmplate" and insert --mm plate--.

Column 25, Line 47: delete "100,000 xg" and insert --100,000xg--.

Column 28, Line 22: delete "A10" and insert --A11--.

UNITED STATES PATENT AND TRADEMARK OFFICE
CERTIFICATE OF CORRECTION

PATENT NO. : 5,700,823
DATED : December 23, 1997
INVENTOR(S) : Klaus Peter Hirth, et al.

It is certified that error appears in the above-indentified patent and that said Letters Patent is hereby corrected as shown below:

Column 29, Line 62: delete "$Na_2S_4$" and insert --$Na_2SO_4$--.

Column 30, Line 10 : delete "$NaHC_3$" and insert --$NaHCO_3$--.

Column 30, Line 11: delete "$Na_2S_4$" and insert --$Na_2SO_4$--.

Column 31, Line 33: delete "(s) and insert --2H(s)--.

Column 32, Line 38: delete "$P_f$" and insert --$R_f$--.

Column 32, Line 47: delete "$R_f 0.165$" and insert --$R_f=0.165$--.

Column 32, Line 56: delete "$R_f 0.323$" and insert -- $R_f=0.323$--.

Column 33, Line 9: delete "$CH_2C12$" and insert --$CH_2Cl_2$--.

Column 35, Line 60: delete "$C_{16}H_{15}N_3O_3$" and insert --$C_{16}H_{15}N_3O_5$--.

Column 36, Line 53: delete "for additional" and insert --for an additional--.

Column 37, Line 38: delete "3,4-dimethyl-i" and insert --3,4-dimethyl-l--.

Column 40, Line 8: delete "$C_{24}H21N_3O_2$" and insert --$C_{24}H_{21}N_3O_2$--.

UNITED STATES PATENT AND TRADEMARK OFFICE
CERTIFICATE OF CORRECTION

PATENT NO. : 5,700,823
DATED : December 23, 1997
INVENTOR(S) : Klaus Peter Hirth, et al.

It is certified that error appears in the above-indentified patent and that said Letters Patent is hereby corrected as shown below:

Column 41, Line 61: Claim 6, delete "hydroxycrotoamide, pharmaceutically" acceptable salts thereof" and insert --hydroxycrotoamide, and pharmaceutically acceptable salts thereof--.

Signed and Sealed this

Sixteenth Day of June, 1998

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,700,823
DATED : December 23, 1997
INVENTOR(S) : Klaus Peter Hirth, et al It is certified that error appears in the above-identified patent and that said Letters Patent is hereby corrected as shown below:

On the title page, item [75](inventors): delete the following inventors: "Gyorgy Keri, Budapest, Hungary; Istvan Szekely, Dunakeszi, Hungary; Tamas Bajor, Budapest, Hungary; Janis Haimichael, Budapest, Hungary; Laszlo Orfi, Budapest, Hungary; Alex Levitzki; Aviv Gazit, both of Jerusalem, Israel"

Signed and Sealed this

Fourteenth Day of September, 1999

*Attest:*

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,700,823
DATED : Dec. 23, 1997
INVENTOR(S) : Klaus Peter Hirth, et la It is certified that error appears in the above-identified patent and that said Letters Patent is hereby corrected as shown below:

On title page, item [73], delete the following assignees: "Biosignal L.T.D., Budapest, Hungary; Yissum Research Development Company, Hebrew University of Jerusalem, Jerusalem, Israel."

Signed and Sealed this

Eleventh Day of April, 2000

Attest:

Q. TODD DICKINSON

*Attesting Officer*     *Director of Patents and Trademarks*